United States Patent
Galstian

(10) Patent No.: US 10,098,727 B1
(45) Date of Patent: Oct. 16, 2018

(54) TUNEABLE LIQUID CRYSTAL LENS INTRAOCULAR IMPLANT AND METHODS THEREFOR

(75) Inventor: Tigran Galstian, Québec (CA)

(73) Assignee: LensVector Inc., San Jose, CA (US)

( * ) Notice: Subject to any disclaimer, the term of this patent is extended or adjusted under 35 U.S.C. 154(b) by 489 days.

(21) Appl. No.: 13/369,806

(22) Filed: Feb. 9, 2012

Related U.S. Application Data

(60) Provisional application No. 61/441,863, filed on Feb. 11, 2011.

(51) Int. Cl.
A61F 2/16 (2006.01)

(52) U.S. Cl.
CPC .......... *A61F 2/1637* (2013.01); *A61F 2/1613* (2013.01); *A61F 2/1624* (2013.01); *A61F 2/1627* (2013.01)

(58) Field of Classification Search
CPC ...... A61F 2/147; A61F 2/1613; A61F 2/1635; A61F 2/1616; A61F 2/1618; A61F 2/1624; A61F 2/1627; A61F 2/1637
USPC ................................. 623/4.1, 6.22
See application file for complete search history.

(56) References Cited

U.S. PATENT DOCUMENTS

| | | | |
|---|---|---|---|
| 6,576,013 B1 | 6/2003 | Budman et al. | |
| 6,638,304 B2 | 10/2003 | Azar | |
| 2006/0164593 A1* | 7/2006 | Peyghambarian et al. | ... 349/200 |
| 2007/0139333 A1 | 6/2007 | Sato et al. | |
| 2007/0229754 A1 | 10/2007 | Galstian et al. | |
| 2008/0208335 A1* | 8/2008 | Blum et al. | ............ 623/6.22 |
| 2009/0204207 A1* | 8/2009 | Blum | ............. G02C 7/08 623/4.1 |
| 2009/0245074 A1 | 10/2009 | Tseng | |

FOREIGN PATENT DOCUMENTS

WO  WO 2007/098602 A1  9/2007
WO  WO 2009/146530 A1  12/2009

OTHER PUBLICATIONS

A.F.Naumov et al., Control optimization of spherical modal liquid crystal lenses, Optics Express, pp. 344-352, Apr. 26, 1999, vol. 4, No. 9
A.F.Naumov. M.Yu Loktev, I.R.Guralnik and G.Vdovin, Liquid-Crystal Adaptive Lenses with Modal Control, Optics Letters. pp. 992-994, Jul. 1. 1998, vol. 23, No. 13, Optical Society of America.
Faith A. Hayden, Electronic IOLs: The future of cataract surgery, EW Feature, IOLs Feb. 2012, p. 58-60.
(Continued)

*Primary Examiner* — Howie Matthews
(74) *Attorney, Agent, or Firm* — Anglehart et al.

(57) ABSTRACT

An intraocular adaptive lens prosthesis apparatus is provided. In some implementations the apparatus includes a tunable liquid crystal lens encapsulated in the intraocular prosthesis with control electronics and a power source. In other implementations the apparatus includes a tunable liquid crystal lens encapsulated in the intraocular prosthesis with a control signal receiver while an external control electronics package transmits the control signal. The tunable liquid crystal lens is driven in response to a stimulus signal to provide accommodation. In some embodiments the tunable liquid crystal device corrects other visual shortcomings of the natural eye.

22 Claims, 21 Drawing Sheets

(56) References Cited

OTHER PUBLICATIONS

Gleb Vdovin, Mikhail Loktev, Alexander Naumov, On the possibility of intraocular adaptive optics, Optics Express, Apr. 7, 2003, pp. 810-817, vol. 11, No. 7.
Mao Ye, Bin Wang, Susumu Sato; Liquid crystal lens with focus movable in focal plane; Optics Communications; vol. 259, Issue 2, Mar. 15, 2006, pp. 710-722.
Nicolas Fraval et al., Liquid crystal lens auto-focus extended to optical image stabilization for wafer level camera, Proc. SPIE 7930, MOEMS and Miniaturized Systems X, 793009, Feb. 14, 2011.
Samuel Masket, Accommodating IOLs: Emerging Concepts and Designs, Cataract & Refractive Surgery today, Jul. 2004. pp. 32-36.
Susumu Sato, Applications of Liquid Crystals to Variable-Focusing Lenses, Optical Review vol. 6, No. 6 (1999) 471-485.
Susumu Sato, Liquid-Crystal Lens-Cells with Variable Focal Length, Japanese Journal of Applied Physics, vol. 18 No. 9, Sep. 1979, pp. 1679-1684.

\* cited by examiner

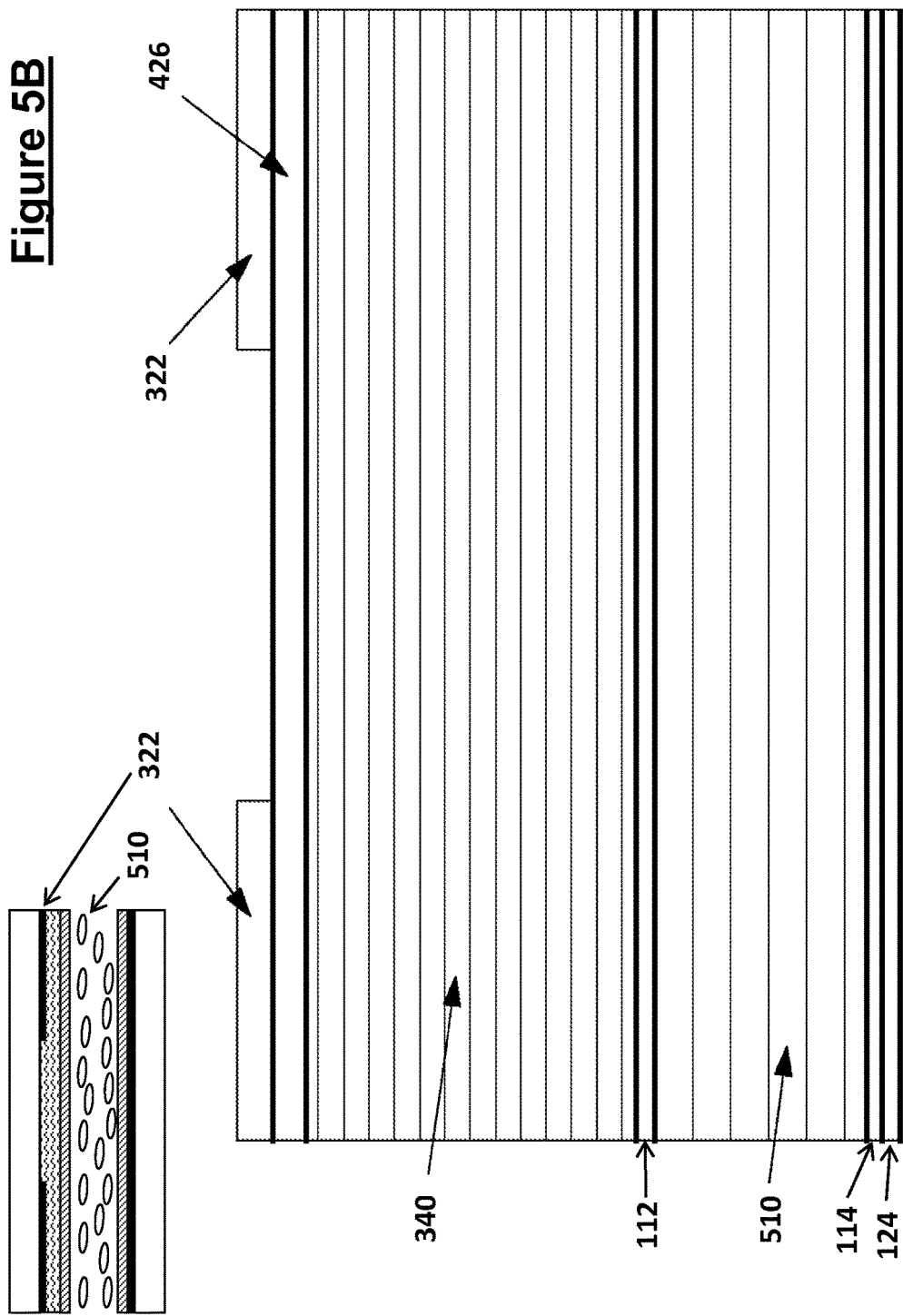

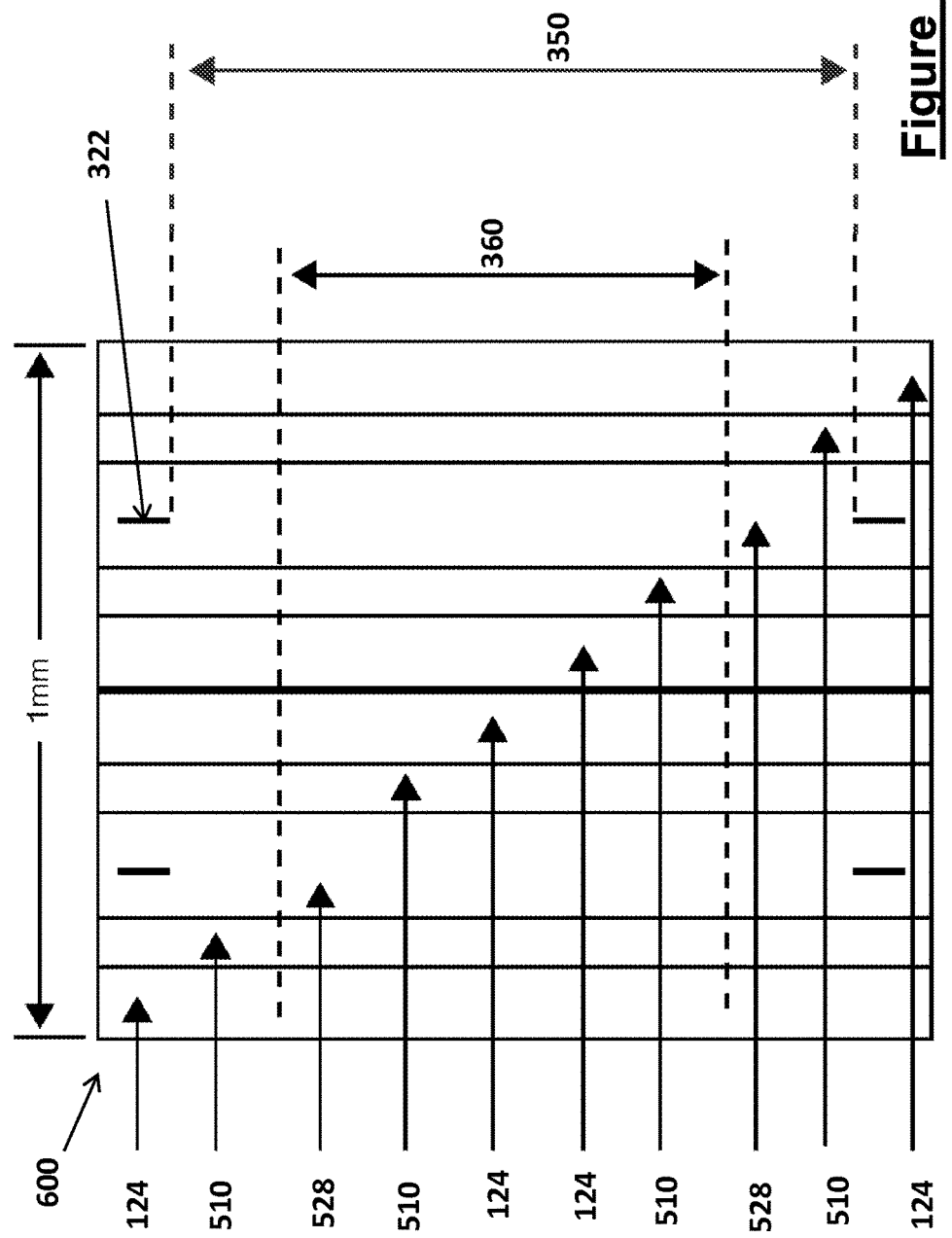

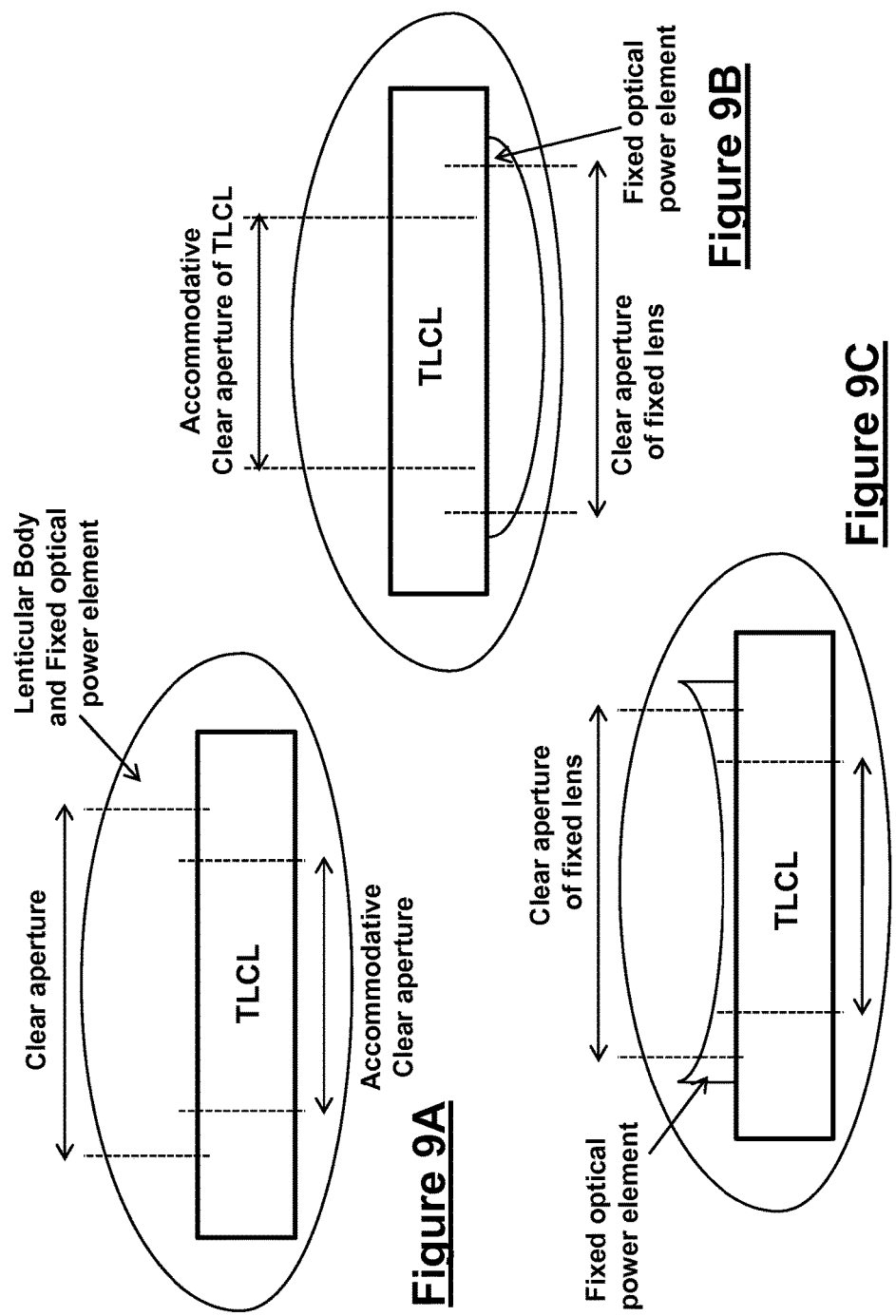

TUNEABLE LIQUID CRYSTAL LENS INTRAOCULAR IMPLANT AND METHODS THEREFOR

RELATED APPLICATIONS

This application is a non-provisional of, and claims priority from, U.S. 61/441,863 of same title filed Feb. 11, 2011, the entirety of which is incorporated herein by reference.

TECHNICAL FIELD

This invention relates to vision correction, and in particular to active intraocular implant assisted vision apparatus and methods therefor.

BACKGROUND

Various medical conditions are addressed by fitting an eye with an intraocular lens to replace a natural crystalline lens of the eye. Such medical conditions include aging effects, or can result from accidents or from exposure to atypical environmental conditions.

For example, development of a cataract is a common condition experienced with age. The eye is typically fitted with an intraocular lens during cataract surgery. A goal of cataract surgery has long been to provide, postoperatively, unaided (without wearing glasses) high-quality distance, intermediate, and near vision.

For many years, basic attempts to restore vision have included surgically emptying a capsular bag in which the natural crystalline lens of the eye resides and refilling it with an accommodating polymer that matches the behavior of a juvenile lens. While such attempts have received considerable attention an effective actualization remains elusive today in part because properties of homogeneous polymers are insufficient to mimic properties of an inhomogeneous natural crystalline lens. In an article entitled "Accommodating IOLs: Emerging Concepts and Designs" published July 2004 in Cataract & Refractive Surgery Today, Samuel Masket MD describes difficulties in characterizing a crystalline lens in situ, which is subject to forces exerted by adjoining tissues, leading to an inability to create an implant having desired properties under forces exerted by adjoining tissues postoperatively.

Emptying the capsular bag may induce some damage to tissues other than the crystalline lens. The healing process includes transient and permanent changes in adjoining tissues. Postoperative changes in adjoining tissues vary with the nature of the implant material and its contact with an anterior capsule of the eye. Masket further appraises of a need to control postoperative reactions of lens epithelial cells in order to reduce the tendency for fibrometaplasia, typically observed for anterior subcapsular lens epithelial cells after implant surgery. As well, any crystalline lens characterization is necessarily performed on an imperfect lens slated for invasive medical removal with the desire of providing a perfect intraocular prosthesis postoperatively. Even if a characterization of the crystalline lens from an earlier age would have been available, the surrounding tissues also vary with age rendering such characterization insufficient.

Implanting a fixed focus (monofocal) lens has been attempted in the prior art with limited degree of success. Postoperatively the combination of the remaining adjoining tissues and fixed focus lens provide a limited degree of accommodation (controlled focus variability) compared to the juvenile natural lens. It has been found that such monofocal prosthesis combinations may provide between 0.5 to 1.5 diopter pseudoaccommodation after surgery. In comparison, research by Scheiman, Mitchell and Wick, Bruce in Clinical Management of Binocular Vision, Lippincott, N.Y., 1994 suggests that on average a juvenile lens provides 18 diopters variability in average amplitude of accommodation. The average amplitude of accommodation at a given age may be estimated by Hofstetter's formula: 18.5 minus one third of the patient's age in years. Therefore, while such an intraocular implant may provide clearer vision post cataract operation, the limited degree of post operative accommodation requires additional visual aids such as glasses or contact lenses.

Musket provides a survey of intraocular lens devices characterized by at least one movable lens optic within the capsular bag. A change in the position of a single optic providing focus variability, although simple in design, is considered to be insufficient to provide accommodation over a wide diopter range. In addition, it is recognized that the flexibility of the capsular bag remains an important performance aspect for such implant designs. Single optic flexible prostheses which fill the entire capsular bag and remain stationary while changing an anterior/posterior dimension to vary optical power subject to forces provided by the ciliary body are also considered insufficient. Some attempts suffer from material incompatibilities while others remain theoretical. Dual optic prostheses have been implanted however suffer from low optical power variability in the range of 2.5 diopters.

Tunable Liquid Crystal (TLC) optical devices are described, for example, in commonly assigned International Patent Application WO/2007/098602, which claims priority from U.S. 60/778,380 filed on Mar. 3, 2006, both of which are incorporated herein by reference. TLC optical devices are flat multi-layered structures having a Liquid Crystal (LC) layer. The liquid crystal layer has a variable refractive index which changes in response to an electric field applied thereto. Applying a non-uniform (spatially modulated) electric field to such liquid crystal layer, provides a liquid crystal layer with a non-uniform (spatially modulated) index of refraction. Moreover, liquid crystal refractive index variability is responsive to a time variable electric field. In general, TLC's are said to have an index of refraction which varies as a function of an applied drive signal producing the electric field.

With an appropriate geometry, a variety of optical components employing TLC optical devices can be built, for example: a tunable lens, a corrective optical element, an optical shutter, iris, etc. Tunable Liquid Crystal Lenses (TLCLs) provide significant advantages being thin and compact. The performance of TLC lenses may be measured by a multitude of parameters, including: a tunable focus range, optical power (diopter) range, power consumption, transmittance, etc. The optical power of a TLC lens refers to the amount of ray bending that the TLC lens imparts to incident light (and more specifically to an incident light field representative of a scene) passing therethrough.

Recently tunable liquid crystal lenses have been proposed for use in active accommodation. For example:

A notable prior art experimental attempt at providing a TLC lens is Naumov et al., "Liquid-Crystal Adaptive Lenses With Modal Control" Optics Letters, Vol. 23, No. 13, p. 992, Jul. 1, 1998, which describes a one hole-patterned layered structure defined by a non-conductive center area of an electrode covered by a transparent high resistivity layer. With reference to FIG. 1, TLC 100 includes: top 102 and bottom 104 substrates, and a middle Liquid Crystal (LC) layer 110 sandwiched between top 112 and bottom 114 liquid crystal orienting layers. LC orienting layers 112/114 include polyimide coatings rubbed in a predetermined direction to align LC molecules in a ground state, namely in the absence of any controlling electric field. The predetermined orientation angle of LC molecules in the ground state is referred to herein as the pre-tilt angle. The average orientation of long liquid crystal molecular axes in a liquid crystal layer is referred to as a director. An electric field is applied to the LC layer 110 using a uniform bottom transparent conductive electrode layer 124 of Indium Tin Oxide (ITO), and the top hole-patterned conductive ring electrode layer 122 of Aluminum (Al). The low resistivity hole-patterned conductive layer 122 together with the high resistivity layer 126 immediately below the hole-patterned conductive layer 122 form an electric field shaping control layer 128. In accordance with Naumov's approach, the reactive impedance of the LC layer 110 which has capacitance and the complex impedance of the high resistivity layer 126 play a strong role, requiring driving the TLCL via specific voltage and frequency parameter pairs to minimize root means square deviation from a parabolic phase retardation profile for corresponding desired optical power settings (transfer function).

Unfortunately, from a manufacturing perspective it is very difficult to produce, with useful consistency, the required sheet resistance of high resistivity material having high optical transparency for the highly resistive layer 126. It happens that, for millimeter size lenses, the value of R_s, for almost all known solid state materials, is in the middle of an electrical conductivity transition (percolation) zone, where the sheet resistance has a very drastic natural variation with layer 126 geometry. Therefore in practice it is very difficult to produce such TLCLs consistently. Different TLCL's of the same manufacturing batch have slightly different resistances. Such sheet resistance variability coupled with the fact that control is very dependent on the precise LC cell thickness, leads to each such individual TLC lens requiring separate calibration and drive. Two identical such TLC lenses must be used together, with cross-oriented directors, to act on unpolarized natural light.

Despite these drawbacks, in an article published on 7 Apr. 2003 in Optics Express, Vol. 11, No. 7, pp. 810-817 entitled "On the possibility of intraocular adaptive optics", Naumov et al. presents a theoretical treatise considering the technical possibility of an adaptive contact lens and adaptive eye lens implant using the modal liquid crystal lens described above as a modal liquid-crystal wavefront corrector aimed to correct accommodation loss of the human eye. However, a breadboard demonstrator described, having a 5 mm optical (ring electrode) aperture, provided only some accommodation improvement of about 3 diopters. While amplitude and spectral composition of an applied unipolar AC voltage is theorized for controlling both optical power and radial aberrations of the modal lens, reduction to practice is difficult in view of the specific voltage and frequency parameter pairs required for driving the TLCL to minimize root means square deviation from the parabolic phase retardation profile. Naumov also theorizes control of azimuthal optical aberration components being realized by splitting the annular control ring (122) into sectors with independent control signal components applied to each sector. However, experiments performed by Naumov in providing wireless control have shown that the modal liquid-crystal wavefront corrector cannot develop the required voltage amplitudes across the liquid crystal layer using inductive control and that capacitive control results in rather large voltages being developed in the order of 10V while providing only a limited optical power range of 3 diopters. These results are understood as a direct consequence of the reactive impedance of the LC layer 110 which has capacitance and the complex impedance of the high resistivity layer 126 which play a strong role favoring capacitive wireless control. It remains unclear how capacitive control may be used for actively driving a segmented annular ring electrode to control azimuthal optical aberration components because of complex capacitive interactions between capacitive drive and inter segment capacitances. Photoelectric control while mentioned, is dismissed by Naumov due to a large 1 mW optical source required to shine substantially into the eye during operation. Moreover, at page 814 lines 3 to 4, Naumov et al. expressly state "[their] belie[f that] no wires can be used in the human eye and no battery can be embedded into the lens [prosthesis]."

Another prior art attempt is described by Azar in U.S. Pat. No. 6,638,304 published 28 Oct. 2003 entitled "Vision Prosthesis". Azar builds on fixed focus optic implants described hereinabove and concludes that multifocal lens implants are less than desirable introducing aberrations due to an inability to select a desired optical axis as typically possible with bifocal glasses because the implanted lens does not permit relative motion between the pupil and the implanted corrective lens. In contrast to Naumov, Azar does not present experimental results based on any actualized tunable liquid crystal lens. Miniaturization of eye glasses sized liquid crystal lenses relied upon by Azar to the size of the capsular bag typically 9 mm by 4 mm has been found impractical for the following reasons: Some embodiments described by Azar (at column 5 line 59 to column 6 line 6) include multitudes of individually addressable electrodes for example arranged concentrically or in a grid pattern to provide spatial modulation together with a liquid crystal layer. Miniaturization of such embodiments is extremely complicated because the numerous traces required to drive each electrode, would introduce electric field components which would impede consorted operation of liquid crystal molecules in the liquid crystal layer to provide a lens of miniature dimensions. In other embodiments (presented in column 6 lines 11 to 17) liquid crystal molecular reorientation is described to employ a magnetic field generated by a current carrying coil. However, power requirements of such a coil are impractical for intraocular prostheses. Other embodiments (presented at column 5 lines 45 to 58) employ electric field drive achieved via differential DC voltages maintained across multiple electrodes arrayed over a liquid crystal layer. Practical application of DC voltage drive is very limited because applied DC voltages have been found to degrade liquid crystal properties. Yet other embodiments (presented at column 6 lines 32 to 39) describe individual addressable lenslet arrays with individual electrodes for each lenslet. However, a very large number of individual lenslets would be required to achieve a smooth refractive index variation across the pupil, correspondingly the inert material separating each lenslet would cover a substantial area of the pupil, as well dispensing the very small amounts of liquid crystal material required for each lenslet during manufacture is limited by surface tension of the liquid crystal material. In contrast, experimental results provided by Naumov, and operational results of tunable liquid crystal lenses presented in commonly assigned International Patent Application WO/2007/098602, which claims priority from U.S. 60/778, 380 filed on Mar. 3, 2006, both of which are incorporated herein by reference, show tunable liquid crystal lens reduction to practice using few, typically one spatially non-uniform patterned electrode generating a spatially modulated electric field generated by few, in some embodiments one AC drive signal.

Moreover, the nature of the variability of the index of refraction in response to an applied electric field depends on the physical properties of TLC multi-layered structure, including properties of the liquid crystal layer material, material properties of other layers, geometry, etc. A quasi-linear "functional" relationship between the drive signal applied and the index of refraction of a TLC optical device exists over a usable drive signal variability range. However, the overall relationship is non-linear: In some TLC devices, a physical non-linear effect, known as disclination, is observed as the liquid crystal molecules begin to align with the electric field from a ground state orientation to an orientation dictated by the electric field. In broad terms, when the applied electric field is essentially homogenous, non-linearity means that the change in optical property (e.g. index of refraction) per unit drive signal change varies over the range of optical property change of the optical device. Such disclinations cause optical defects and aberrations in the lens which persist with gradual voltage adjustments necessarily employed in tuning. In "Liquid Crystal Lens with Focus Movable in Focal Plane", published 2006, in Optics Communications 259, pp. 710-722, Sato specifically points out on page 711 mid page in the left hand column problems with divided electrode structures described by Azar: "The problem in the divided-electrode structure is that disclination lines occur if the potential differences among adjacent subelectrodes become large . . . ".

With reference to column 6 lines 18 to 26, Azar, based on then known low optical power liquid crystal lenses, addresses optical power insufficiency by employing micromechanical motors, alternatively proposes employing a curved liquid crystal lens having a baseline curvature performing gross correction while local liquid crystal reorientation-induced refractive index variations are employed to fine-tune the gross correction. To date manufacturing LC structures on curved substrates is impractical.

In U.S. Pat. No. 6,576,013 filed 8 Jan. 2002, entitled "Eye prosthesis" Budman et al. describe a cosmetic hard contact lens containing electronics for displaying an iris and pupil image on a color liquid crystal array display device embedded in the hard contact lens. The hard contact lens is not a (functional) replacement for a natural eye lens and is not employed in vision restoration.

SUMMARY

It has been discovered that a temperature dependence of tunable liquid crystal optical devices combined with the temperature control provided by a human body permits operational simplifications in controlling a tunable liquid crystal lens employed as an intraocular prosthesis.

In accordance with an aspect of the present proposed solution a biocompatible intraocular lens prosthesis is provided configured to fit within a capsular bag of an eye from which a natural eye lens is removed, intraocular lens which provides an optical power accommodation larger than 3.5 diopters. A typical capsular bag maximum available cavity size is about 9 mm in diameter and has a thickness of about 4 mm.

In accordance with another aspect of the proposed solution an intraocular lens prosthesis is provided operating at low voltages, typically operating below 7V, while providing an adequate accommodation range.

In accordance with a further aspect of the proposed solution an intraocular lens prosthesis is provided having an accommodative clear aperture greater than 3 mm, typically more than 4.5 mm.

In accordance with a further aspect of the proposed solution an intraocular lens prosthesis is provided having low power consumption below 150 µW, typically between 10 µW and 100 µW.

In accordance with a further aspect of the proposed solution an intraocular lens prosthesis is provided having a spectral transmittance fidelity greater than 75% in the visible spectrum, typically 90%.

In accordance with a further aspect of the proposed solution an intraocular lens prosthesis is provided having optical power change transition time in the order of 0.4 s.

In accordance with a further aspect of the proposed solution there is provided an intraocular implant apparatus for replacing a natural lens of an eye, the apparatus comprising: an encapsulated tunable liquid crystal optical device including: a tunable liquid crystal lens having a variable optical power having an accommodation clear aperture; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal; and a transparent encapsulating material configured to provide a fixed optical power element for augmenting said optical power of said tunable liquid crystal lens, said encapsulating material forming a pronounced lenticular shape at least over said accommodation clear aperture of the tunable liquid crystal lens, said encapsulating material encapsulating said drive signal generator, tunable liquid crystal lens controller, said power storage and said sensor component arranged about the periphery of said tunable liquid crystal lens.

In accordance with a further aspect of the proposed solution there is provided an intraocular implant apparatus for replacing a natural lens of an eye, the apparatus comprising: an encapsulated tunable liquid crystal optical device including: a bipolar tunable liquid crystal lens having an optical power varying between a negative optical power and a positive optical power; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal.

In accordance with a further aspect of the proposed solution there is provided an intraocular implant apparatus for replacing a natural lens of an eye, the apparatus comprising: an encapsulated tunable liquid crystal optical device including: a bipolar tunable liquid crystal lens having a variable optical power; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal in response to a stimulus external to said optical device.

In accordance with a further aspect of the proposed solution there is provided a magnetic bead implant having a suitable biocompatible composition/material.

In accordance with yet another aspect of the proposed solution there is provided a method calibrate magnetic bead location by employing a test pattern and eyelid gestures.

BRIEF DESCRIPTION OF THE DRAWINGS

The invention will be better understood by way of the following detailed description of embodiments of the invention with reference to the appended drawings, in which:

FIG. 5B is a schematic diagram illustrating another equipotentials distribution for a tunable liquid crystal lens subjected to a spatially invariant electric field in accordance with the proposed solution;

FIG. 6 is a schematic diagram illustrating a dual full tunable liquid crystal lens structure in accordance with the proposed solution;

FIG. 9A is schematic diagram illustrating an encapsulated tunable liquid crystal lens in accordance with the proposed solution;

FIG. 9B is schematic diagram illustrating an encapsulated tunable liquid crystal lens having a fixed optical power positive lens element deposited thereon in accordance with the proposed solution;

FIG. 9C is schematic diagram illustrating an encapsulated tunable liquid crystal lens having a fixed optical power negative lens element deposited thereon in accordance with the proposed solution;

DETAILED DESCRIPTION

Tunable Liquid Crystal Lens Structure

In accordance with an aspect of the proposed solution, a variable intraocular optical device is provided for controlling the propagation of light passing therethrough. The sensitivity to the LC cell thickness is alleviated by employing a buffer substrate.

R_s Gradient Softening

Figure 1:
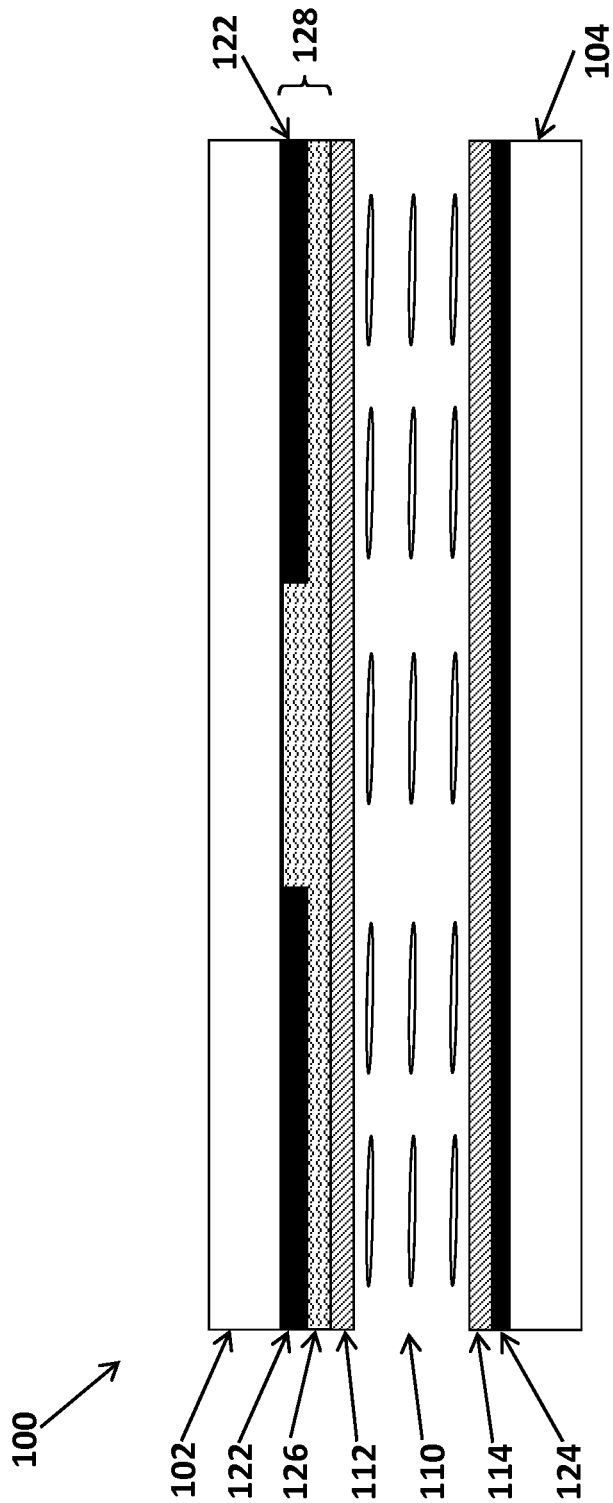
FIG. 1 is a schematic diagram showing a prior art tunable liquid crystal lens device.
Figure 2A:
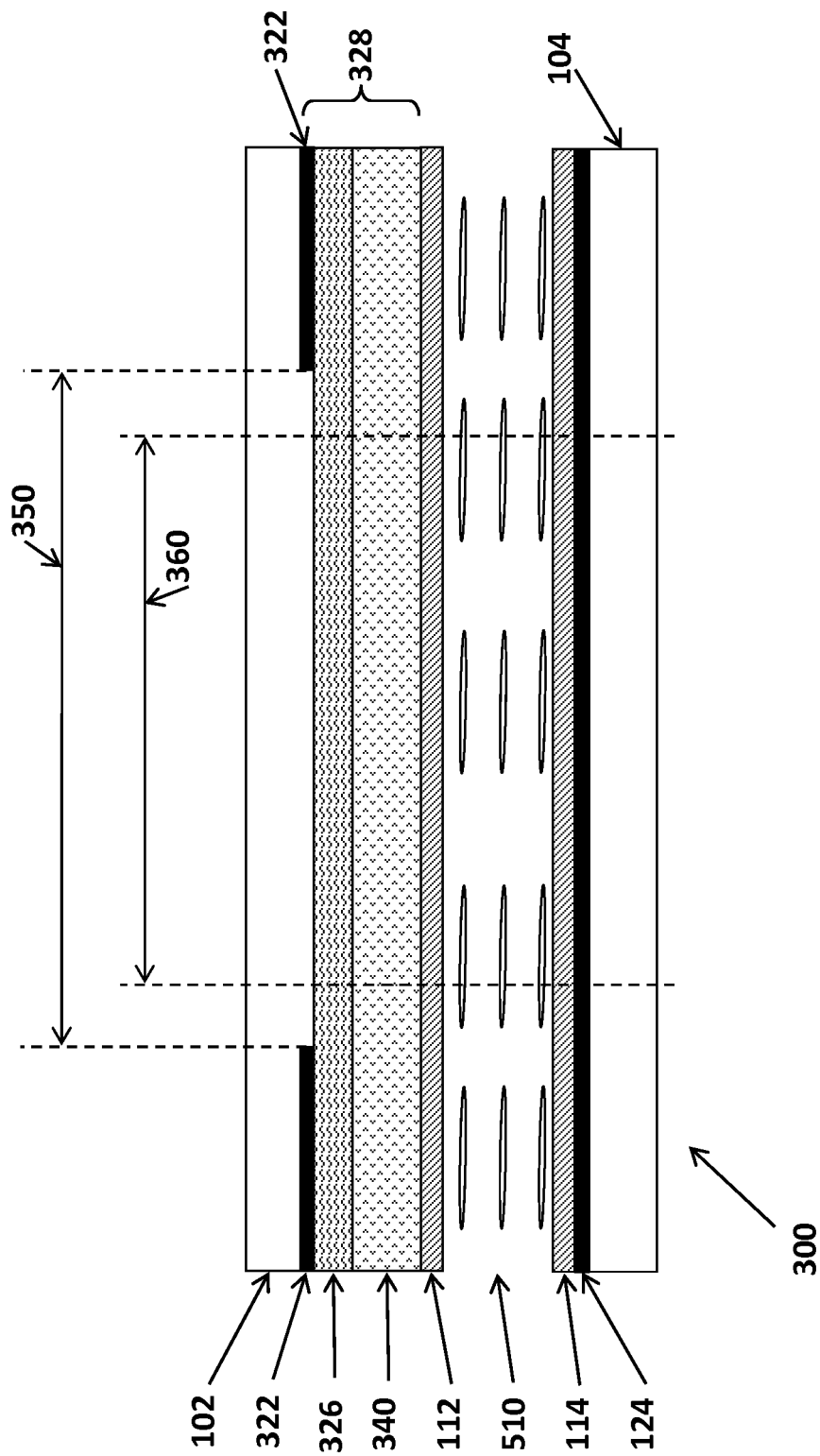
FIG. 2A is a schematic diagram illustrating a tunable liquid crystal lens layered structure in accordance with the proposed solution.

FIG. 2A shows a flat single polarization Tunable Liquid Crystal Lens (TLCL) structure in accordance with the proposed solution. TLCL 300 has an electric field shaping control (layer) substructure 328 including a top fixed hole-patterned conductive ring electrode 322 forming an aperture on top of a Weakly Conductive Layer (WCL) 326 separated from the LC layer 510 by a buffer layer 340. The WCL 326 is either in direct physical contact with the top hole-patterned ring electrode 322 or in electrical contact therewith subject to manufacturing considerations including choice of specific layer materials (not all layer materials bond to each other). The electrical contact provided between the top hole-patterned electrode 322 and the WCL 326 enables the TLCL 300 to employ only two electrodes 322 and 124 to apply a spatially modulated electric field to liquid crystal layer 510. Therefore, TLCL 300 requires a single drive signal minimizing complexity of drive signal generation, drive signal traces and control electronics. The top hole-patterned electrode 322, without limiting the invention, can be made of Al. Other biocompatible/suitable low resistance electrode compositions can be employed, such material selection depending on manufacturing factors familiar to persons of skill in the art of thin wafer fabrication.

In accordance with the proposed solution, buffer layer 340 reduces the sensitivity of the TLCL to LC cell thickness. In accordance with one implementation of the proposed solution, the thickness of buffer layer 340 provides a "buffer spacing" between the WCL 326 and the LC 510, geometry which softens the gradient of the electric field applied. In accordance with another implementation of the proposed solution, "dielectric properties" of the buffer layer 340 softens the gradient of the electric field applied. The invention is not limited to the above examples of buffer layers 340, it is envisioned that in practice buffer layer 340 would be configured to employ a combination of layer thickness and material properties to soften the gradient. Preferred embodiments favor overall thickness reduction of the TLCL 300 minimizing buffer spacing aspects of the buffer layer 340. The buffer layer 340 can further be configured to provide properties typically required of a top substrate of the TLCL 300 structure in order to minimize overall TLCL thickness. For example, buffer layer 340 can include optically transparent (dielectric) materials not limited to polymers, ceramics, etc.

For certainty, the TLCL structure 300 illustrated in FIG. 2A is schematic and not representative of actual proportions of a TLCL structure used as an intraocular prosthesis—layer thicknesses are greatly exaggerated to ease illustration. As well, the hole-patterned electrode 322 aperture is not shown in proportion to the overall TLCL structure 300. The diameter 350 of the hole-patterned electrode aperture is referred to herein as a clear aperture of the TLCL. A smaller diameter 360 represents an accommodative clear aperture and includes a region which refracts incident light at an optical power. The size of the capsular bag of the eye and manufacturing requirements put an upper limit on the overall size of the TLCL, while physical properties of light passing through small apertures limit the accommodative clear aperture 360 to a portion of the clear aperture 350.

Figure 2B:
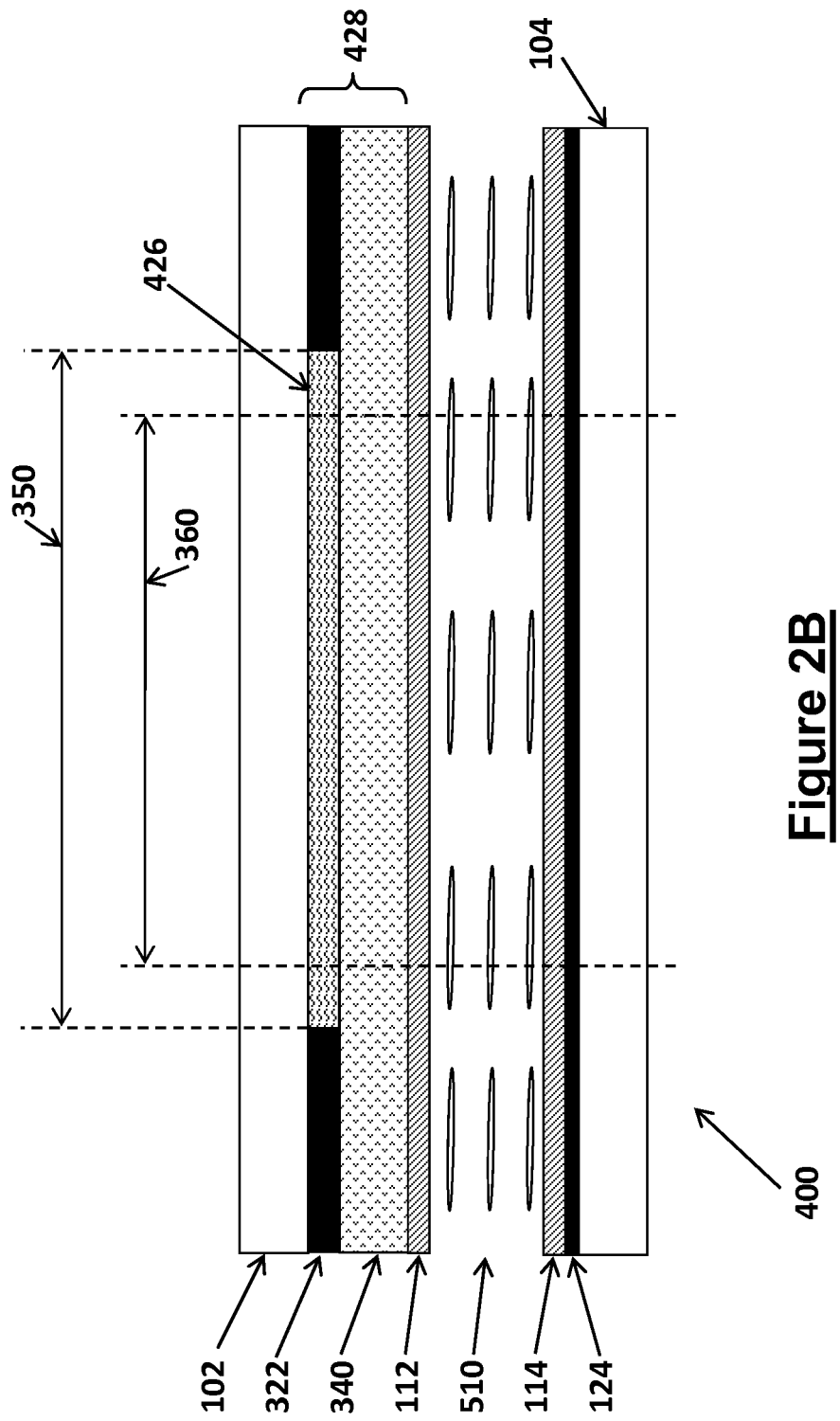
FIG. 2B is a schematic diagram illustrating another tunable liquid crystal lens layered structure having a variable conductivity layer geometry in accordance with the proposed solution.

In accordance with the proposed solution, FIG. 2B illustrates another implementation of tunable liquid crystal lens. TLCL 400 includes a two tier electric field shaping control layer 428. The buffer layer 340 forms a bottom tier immediately adjacent to a variable conductivity layer formed by the top hole-patterned conductive electrode 322 having clear aperture 350 and a weakly conductive layer 426 filling the aperture 350 in the center of the hole-patterned electrode 322. The buffer layer 340 softens the gradient of the electric field applied to the LC 510.

Full TLCL

While FIGS. 2A and 2B describe TLC lens structures configured to control light propagation, such light propagation control is provided only for a single linear light polarization due to the preferential directionality provided by the orienting layers 112/114. Such TLCL structures are said to be polarization dependent referred to as half TLCLs. For operation in natural lighting conditions (sun, lamp), two cross-oriented LC cells are required to control light propagation for two orthogonal polarizations of incident light to provide a polarization independent TLCL. Using a polarizing filter at an angle with respect to a half TLCL can also be used to provide some degree of polarization independence which benefits from a thinner structure, however light throughput is halved.

Prior art optical device geometries proposed by Naumov require the use of two high resistivity layers, which will almost always have different values of R_s and thus the two orthogonal light polarizations will typically not operate synchronously.

In accordance with another aspect of the proposed solution, a TLCL is provided for controlling the propagation of light passing therethrough, the geometry of the TLCL including a common variable conductivity layer employing only one weakly conductive layer for controlling two liquid crystal cells of a polarization independent TLCL.

In accordance with the proposed solution, the polarization dependent geometry presented in FIG. 2B can be extended to provide a polarization independent TLCL structure. Preferably a polarization independent tunable liquid crystal lens intraocular prosthesis is configured to control light propagation for two orthogonally polarized incident light beam components employing a mirrored TLCL structure, referred to as full TLCL.

Figure 2C:
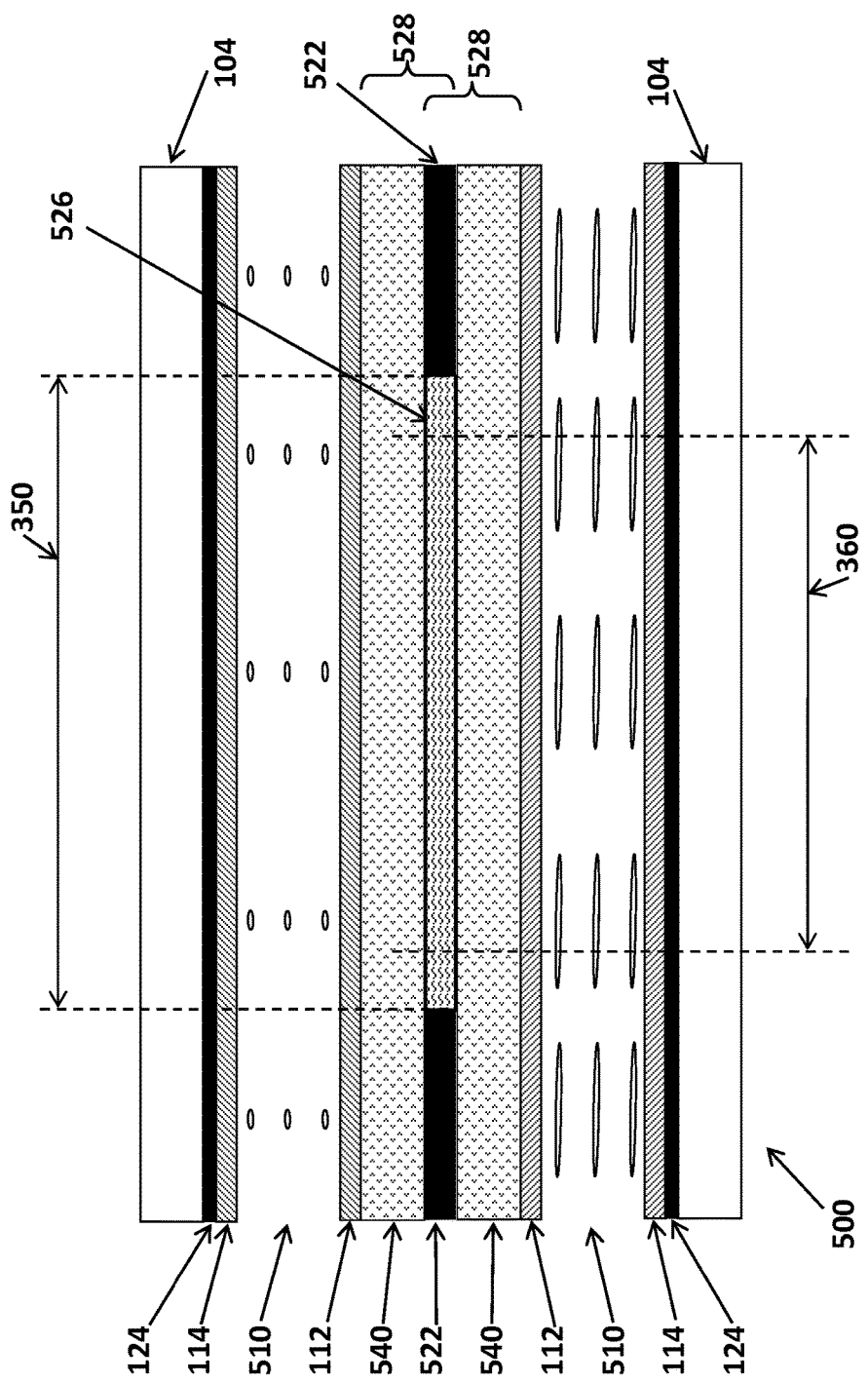
FIG. 2C is a schematic diagram illustrating a polarization independent tunable liquid crystal lens layered structure having a common variable conductivity layer in accordance with the proposed solution.

With reference to FIG. 2C, TLCL structure 500 has a variable conductivity layer including a common hole-patterned mid conductive electrode 522 forming an aperture 350 and a common weakly conductive layer 526 filling the aperture in the center of the common hole-patterned electrode 522. Top and bottom electric field shaping control layers 528 share the variable conductivity layer, each layer 528 employing a respective top and bottom buffer layer 540. Remaining layers are present substantially in mirror fashion about the mid variable conductivity layer shown bearing similar labels according to the functionality provided (qualified by top and bottom identifiers herein below). The central variable conductivity layer is positioned between two LC layers 510. Electrodes 124, to which the drive signal is provided, are located, respectively, adjacent to each LC layer 510, away from the central variable conductivity layer and therefore away from the common hole-patterned conductive electrode 522.

Each one of the two liquid crystal layers 510 employed may be said to have a different LC director orientation as do orienting coatings 112 and 114. Preferably, the two LC layers 510 have directors in substantially orthogonal planes. For example, with the normal of the TLCL layered structure 500 designated as the Z axis, one of the directors might be in the XZ plane while the second director being in the YZ plane.

In accordance with a preferred embodiment, the same WCL 526 is being employed simultaneously for controlling both LC cells. Not only is the TLCL 500 polarization independent, also the focusing of both orthogonal polarizations of the incident natural light is substantially synchronized. In addition, small cell gap variations do not significantly affect overall performance as buffer substrates 540 soften such dependence.

For ease of description of the following TLCL functionality, an abstraction of control electrode structures providing spatial shaping of the driving electric field is made by referring to the electric field shaping control layer 328/428/528. For ease of description, reference to structural elements is made with respect to the half TLCL implementation shown in FIG. 2B. However, the invention is not limited to the implementation shown in FIG. 2B, the functionality described hereinbelow applies to other implementations of the proposed solution such as, but not limited to, those shown in FIGS. 2A and 2C. Preferred implementations include full TLC lens structures 500 illustrated in FIG. 2C.

Operational Characteristics

Tuneability of TLC lenses can be achieved through various drive signal modes, divided for ease of description herein, into: application of a variable voltage amplitude drive signal (fixed frequency amplitude modulation), and application of drive signals having a frequency and an amplitude. References are also made herein to applying a drive signal having a "variable frequency at fixed voltage" (fixed amplitude frequency modulation). A person of ordinary skill in the art would understand references to the "fixed voltage" in the context of a drive signal having a variable frequency, the drive signal having a fixed Root Means Square (RMS) voltage amplitude (Vrms).

Voltage Amplitude Tuneability Control

Figure 3:
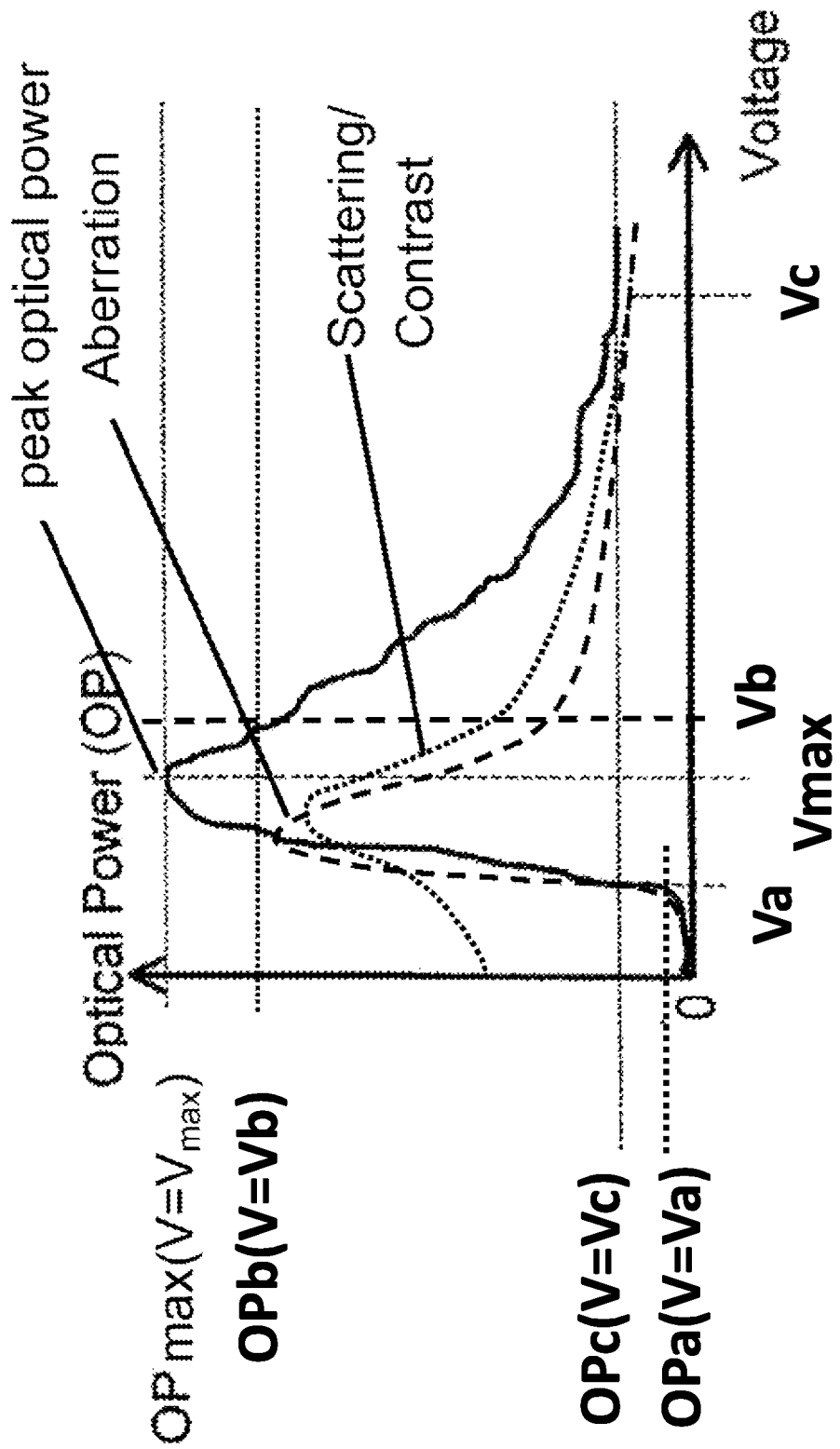
FIG. 3 is a schematic diagram showing a variation of a tunable liquid crystal lens optical power with an applied variable voltage amplitude drive signal.

With reference to FIG. 3, in a TLCL driven via voltage amplitude modulation, LC molecules quickly align in response to an applied spatially modulated electric field created by the application of a voltage amplitude modulated drive signal across electrodes 124, 322. For example, in the case of a positive TLC lens, the highest optical power OPmax of such voltage controlled TLC lens is understood to be achieved as the applied voltage Vmax subjects the LC layer 510 to an electric field having the highest spatial variability for a given TLC geometry 400. This is provided by a strong electric field on the periphery and a weak electric field in the center. This spatial variability of the electric field in turn generates a corresponding non-uniform orientation of LC molecules greater at the periphery and lesser in the center.

Empirically, optical power decreases with increasing applied voltage amplitudes higher than Vmax. Higher voltages employed reduce the spatial variability of the electric field applied to the LC layer 110 compared to that applied by Vmax. The application of higher voltages leads to reorienting LC molecules along electric field lines having lower alignment variability understood as a consequence of saturating the LC molecular reorientation across the LC layer. Aligning LC molecules to an electric field having low variability results in low index of refraction variability across the LC layer and therefore to low optical power, a state employing high driving voltages while providing lower optical power OPc(V=Vc). The transition from Vc to Vmax requires relaxation of the central molecules in the LC layer 510 as voltage is reduced, relaxation which has been experimentally found to be slow. In accordance with prior art techniques, the electric field is simply removed and the LC molecules are allowed to relax (to Va). LC materials have been experimentally found to be slow to respond to the removal of a controlling electric field applied. Therefore, employing high voltages beyond Vmax is a strong drawback from a reverse optical power traverse point of view.

Frequency Control Tuneability

In accordance with a further aspect of the proposed solution, a variable optical device controlling the propagation of light passing therethrough makes use of a frequency dependent material and an electrical signal generator generating a drive signal at a plurality of frequencies and amplitudes to modify a spatial profile of the electric field. An electrical signal generator generates drive signal components at a plurality of different frequency and voltage combinations and supplies a combined drive signal to the electrodes of the TLCL 400 so as to generate an electric field across LC layer 510.

In accordance with an implementation of the proposed solution, the control signal for tuning the tunable liquid crystal lens (TLCL) 400 is provided by a frequency control signal circuit configured to cause the TLC lens 400 to change the optical power and as a result tune the focus of an incident image of a scene.

Modified Weakly Conductive Layer

In accordance with a preferred embodiment of the proposed solution, TLCL 400 employs a weakly conductive layer 426 including a frequency dependent material therein, and frequency control to provide further significant improvements in optical power change speeds and consequently in accommodation transition times. The frequency dependent material enables the WCL 426 to function as a frequency-responsive electric field gradient control layer by shaping the electric field applied to (and experienced) by the LC layer 510. Frequency control is provided by a variable frequency control drive signal circuit configured to cause the TLCL 400 to control light propagation as a function of control drive signal frequency at a selected corresponding RMS voltage amplitude (Vrms).

The material properties of the variable conductivity layer are such that supplying an Alternating Current (AC) drive signal leads to a spatially modulated electric field. With reference to FIG. 2B, the electric field may have a portion substantially defined by the fixed hole-patterned conductive electrode 322, and a portion defined by the frequency dependent material in the weakly conductive layer 426.

The frequency dependent material of the WCL 426 interacts with the electric field and therefore affects the shape the electric field otherwise present between conductive electrodes 124 and 322. For ease of description, however without limiting the invention, the frequency dependent material may include a high dielectric constant material. Functionally, the frequency dependent material of this example has the characteristic of allowing a limited degree of charge mobility therethrough.

The frequency dependent material has a charge mobility which is dependent on the drive signal frequency causing a spatial profile of the electric field to vary as a function of drive signal frequency. Periods of time available for charge to flow within the frequency dependent material are longer at low frequencies which results in higher charge mobility. Similarly, at higher frequencies at the same Vrms amplitude, the electric potential in each positive or negative cycle is applied for shorter periods of time, and the resulting charge flow within the frequency dependent material is correspondingly greatly reduced. Thus "charge mobility" is used to refer to the overall ability of electric charge to (radially) penetrate within the frequency dependent material present in the aperture of the hole patterned electrode within the constraints of the alternating electric drive signal applied. Without loss of generality, for the reminder of the description herein, the weakly conductive layer 426/526 will be referred to as the frequency dependent layer 426.

Frequency dependent materials may consist of a variety of different possible materials. In one embodiment, the frequency dependent material is a thermally polymerizable conductive material, while in another embodiment frequency dependent material is a photo-polymerizable conductive material. Other possibilities include vacuum (or otherwise, e.g. "sol-gel") deposited thin films, high dielectric constant liquids, electrolyte gels, conductive ionic liquids, electronic conductive polymers, materials with electronic conductive nanoparticles, etc. The desired feature of the frequency dependent material being that it has a charge mobility that is frequency dependent. When the frequency dependent material is a thermally or photo-polymerizable conductive material, it may include: a polymerizable monomer compound having at least one ethylenically unsaturated double bond; an initiator that is a combination of UV-vis, NIR sensitive or thermally sensitive molecules; an additive to change the dielectric constant of the mixture, where the additive is selected from the group consisting of organic ionic compounds and inorganic ionic compounds; and a filler to change a viscosity of the mixture. The material may also include an adhesive selective from the group consisting of adhesives sensitive to UV-Vis, adhesives sensitive to NIR and adhesives polymerized using a thermal initiator. An optical elastomer may also be included.

When the frequency dependent material is a high dielectric constant liquid, it may include a transparent liquid material having an epsilon between 2.0 and 180.0 at a relatively low frequency that allows electric charge to move in a frequency dependent manner. When the frequency dependent material is an electrolyte gel material, it may include: a polymer material; an ionic composition; and an ion transporter. When the frequency dependent material is a conductive ionic liquid, it may include an ionic species selected from the group consisting of cholorate, perchlorate, borate, phosphate and carbonate.

While the proposed solution has been described with reference to using a single weakly conductive layer having a frequency dependent material, the invention is not limited to the use of a single frequency dependent material. A number of different frequency dependent materials, not necessarily positioned at a single location relative to the conductive electrodes 124 and 322/522, may be employed in order to shape the electric field of the optical device. As well a frequency dependent layer having a frequency dependent charge mobility that varies along a gradient therethrough can be employed.

TLC Frequency Response

At zero frequency and zero Vrms amplitude, the LC layer 510 is governed by the orienting layers 112 and 114. LC molecules are substantially aligned, for example at 3°. The index of refraction of the LC layer 510 has no variability. No lensing is provided by the LC layer 510, and therefore the TLCL 400 provides zero optical power. This ground state is a passive state governed by the physical properties of the geometry.

Figure 4A:
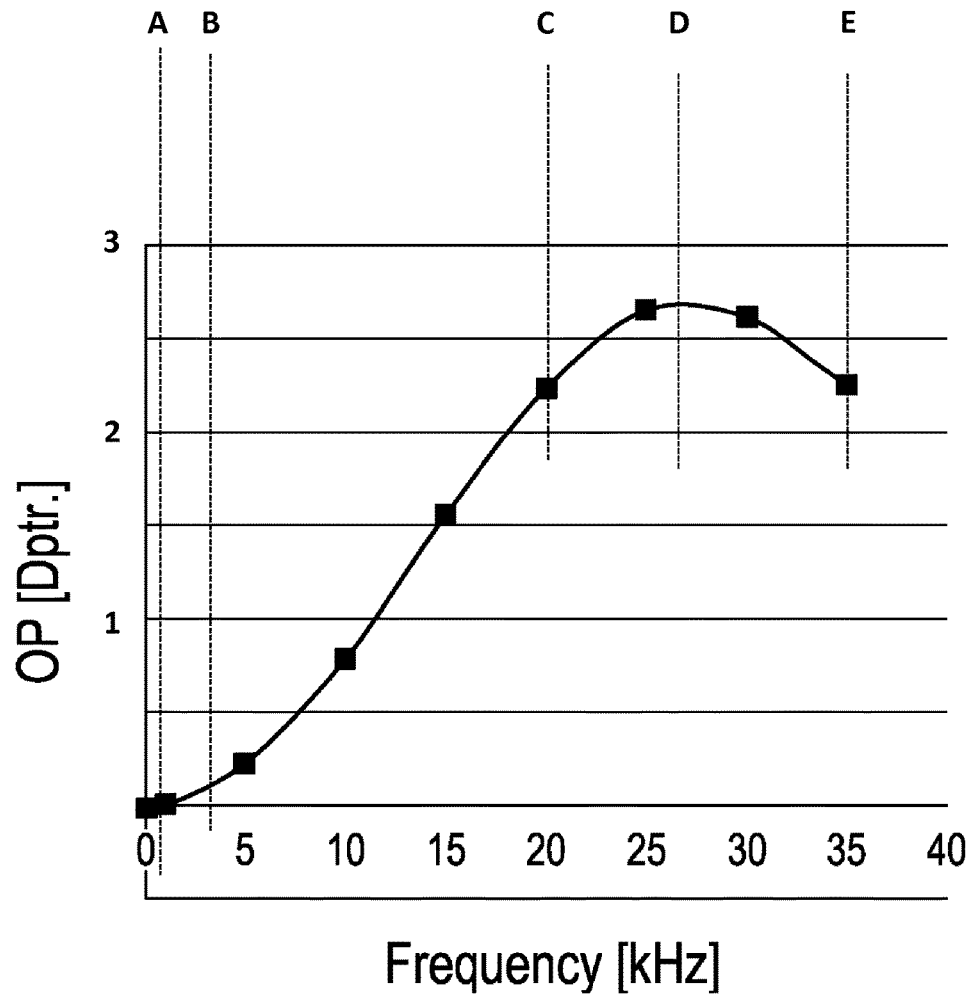
FIG. 4A is a schematic diagram showing a variation of a tunable liquid crystal lens optical power with drive signal frequency at constant root means square voltage amplitude.

FIG. 4A illustrates an observed non-linear optical property response of a tunable LC lens, having a geometry schematically illustrated in FIG. 2B, to a frequency variable drive signal applied at fixed Vrms.

For a given (low) Vrms amplitude beyond an empirically determined threshold, an initial application of a relatively low frequency drive signal creates an effective uniform electrode profile as charge penetrates a good deal across (into) the aperture 350. A corresponding uniform electric field profile, created due to extensive charge penetration into the frequency dependent layer 426, lifts LC molecules across the LC layer 510 out of the ground state to have an initial orientation. The LC molecules will all be reoriented to have a common angular orientation, for example 10° to 15° instead of the pre-tilt angle of about 3°. As described herein above, LC molecules having a common angular orientation, results in an LC layer 510 having a low index of refraction variability, substantially no lensing is provided by the LC layer 510, and therefore the TLCL 400 has negligible optical power. This state is an excited state governed by the properties of the variable conductivity layer including electrode 322 geometry and frequency dependent layer 426 charge mobility as described herein above. This initial excitation state lies in region A-B shown in FIG. 4A and may vary with material properties of the frequency dependent layer, Vrms and TLCL geometry. While the depicted optical property response to applied frequency is shown in region A-B to have a monotonically increasing cusped variability, such variability may not be relied upon for all liquid crystals and/or all Vrms amplitudes. At very low angles such as 4° little torque is applied on the LC molecules by the electric field, and the response has nonlinear effects as a lens is formed. Some LC molecules form alignment domains (disclinations) which can lead to drastic index of refraction variability in this A-B region before charge mobility takes over. As an example, for low Vrms amplitudes a usable low frequency at B can be as low as 100 Hz.

As the frequency of the drive signal is increased beyond B at constant Vrms amplitude, charge penetration into the frequency dependent layer 426 is changed (e.g. reduced). As described herein, as the frequency of the drive signal increases, a nonuniform profile of the electric field develops across the LC layer 510 and the LC molecules have a non-uniform angular orientation. In turn the variability of the index of refraction of the LC layer 510 is non-uniform and the LC layer 510 provides a corresponding lensing effect. Surprisingly, since all of the LC molecules were prealigned by the application of the low frequency B, no disclinations occur (persist) as the lens profile is introduced and the LC molecules efficiently respond to the electric field greatly reducing TLCL lens aberrations.

Within a drive signal frequency range at constant Vrms, between relatively low and relatively high frequencies, the frequency of the driving signal can be varied to provide a gradually changing optical power. In the context of TLCL 400, FIG. 4A depicts a rising variation in optical power. The optical power response beyond B is typically non-linear, for example a maximum optical power is reached at D, about 25 kHz. It is emphasized that maximum optical power being reached at 25 kHz is a consequence of a particular TLCL geometry, particular frequency dependent material selection, and particular low Vrms drive signal amplitude. Low alignment frequencies in the 100 Hz range and maximum optical power in the kHz range advantageously place the necessary frequency generator components into the manufacturable and miniaturizable realm. In operation, power requirements of the application may limit the actual optical power range (used) available.

It has been found that increasing the frequency at constant RMS voltage beyond frequency D leads to a gradual reduction in the optical parameter response. Beyond frequency D at the selected RMS voltage, the high frequency applied has a choking effect on charge flow in the frequency dependent layer 426 and the shape of the electric field applied to LC layer 510 is controlled by other TLCL properties, such as but not limited to: hole-patterned electrode 322 geometry and Vrms. In the case of the TLCL 400, optical power begins to weaken gradually beyond maximum optical power at D up to a frequency E.

Figure 4B:
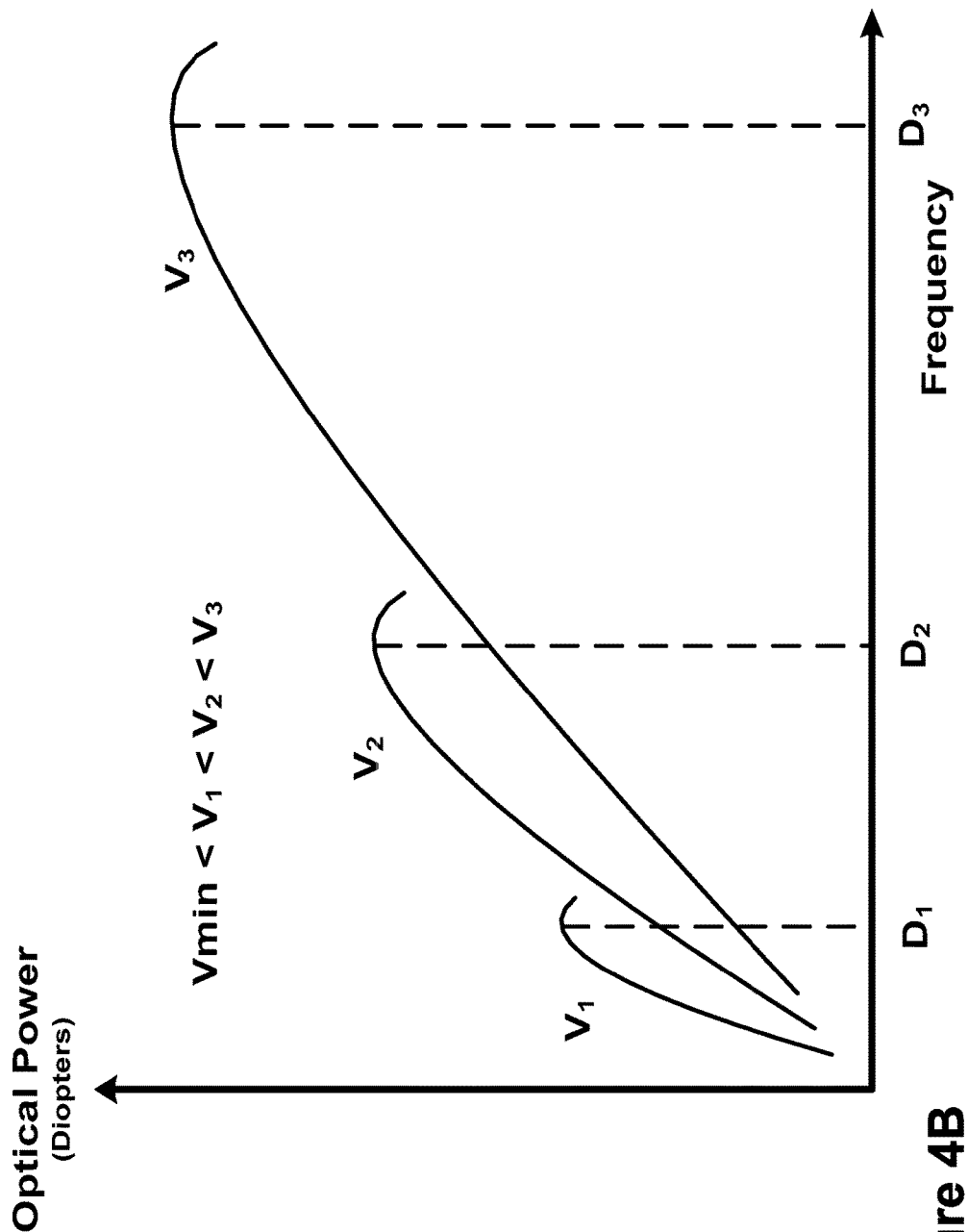
FIG. 4B is a schematic diagram showing a further variation of a tunable liquid crystal lens optical power with drive signal frequency and root means square voltage amplitude.

FIG. 4B shows optical power variability of a frequency controlled TLC lens 400 for different drive signal Vrms amplitudes. For each Vrms amplitude shown, increasing frequency corresponds to an increase (and subsequent decrease) in the optical power of the TLC lens. Depending on the higher Vrms amplitude applied, the alignment frequency B(Vrms) may be higher, the optical power range may have a higher maximum OPmax, that OPmax maximum may occur at a higher frequency D(Vrms) illustrated as D1, D2 and D3 for three different Vrms amplitudes V1, V2 and V3. The choking frequency E(Vrms) may also be higher. Different usable frequency ranges B(Vrms)-D(Vrms) provide different optical power ranges OP(B(Vrms))-OP(D(Vrms)) depending on the Vrms amplitude of the drive signal with substantial overlap at lower frequencies. Such behavior is typical of a TLC lens 400 employing the geometry shown in FIG. 2B and is understood to extend to a TLC lens 500 employing geometry shown in FIG. 2C. Operational parameters of a particular application may limit operability to a subset of Vrms values (range).

For example, the optical power of such a TLC Lens can vary roughly from 8 to 16 diopters. However, operational limitations of a TLCL intraocular prosthesis such as limited size, limited power, operating temperature, biocompatibility, etc. reduce the optical power of a TLCL 500 having an accommodative clear aperture 360 of 4.5 mm to about at least 1.7 diopters. By employing a dual full TLCL 500 structure having an accommodative clear aperture 360 of 4.5 mm, the optical power of such intraocular prosthesis can be at least 3.5 diopters. Reducing the accommodative clear aperture 360 to about 3 mm, the optical power of a single full TLCL 500 can be at least 3.5 diopters, and at least 7 diopters for a dual full TLCL 500 intraocular prosthesis. A dual full TLCL structure 600 is illustrated schematically in FIG. 6.

While implementations of the proposed solution have been described employing a single drive signal having a single variable frequency drive signal component, the invention is not limited thereto. A multitude of variable frequency drive signal components can be mixed together and applied simultaneously to create a desired profile for the electric field (via the frequency dependent material). In one implementation the multitude of frequencies combine to produce a pulse width modulated signal for which the filing factor can be varied. The filling factor can be modified to change the amount of high frequency content in the signal.

Amplitude Modulation Equipotentials

Figure 5A:
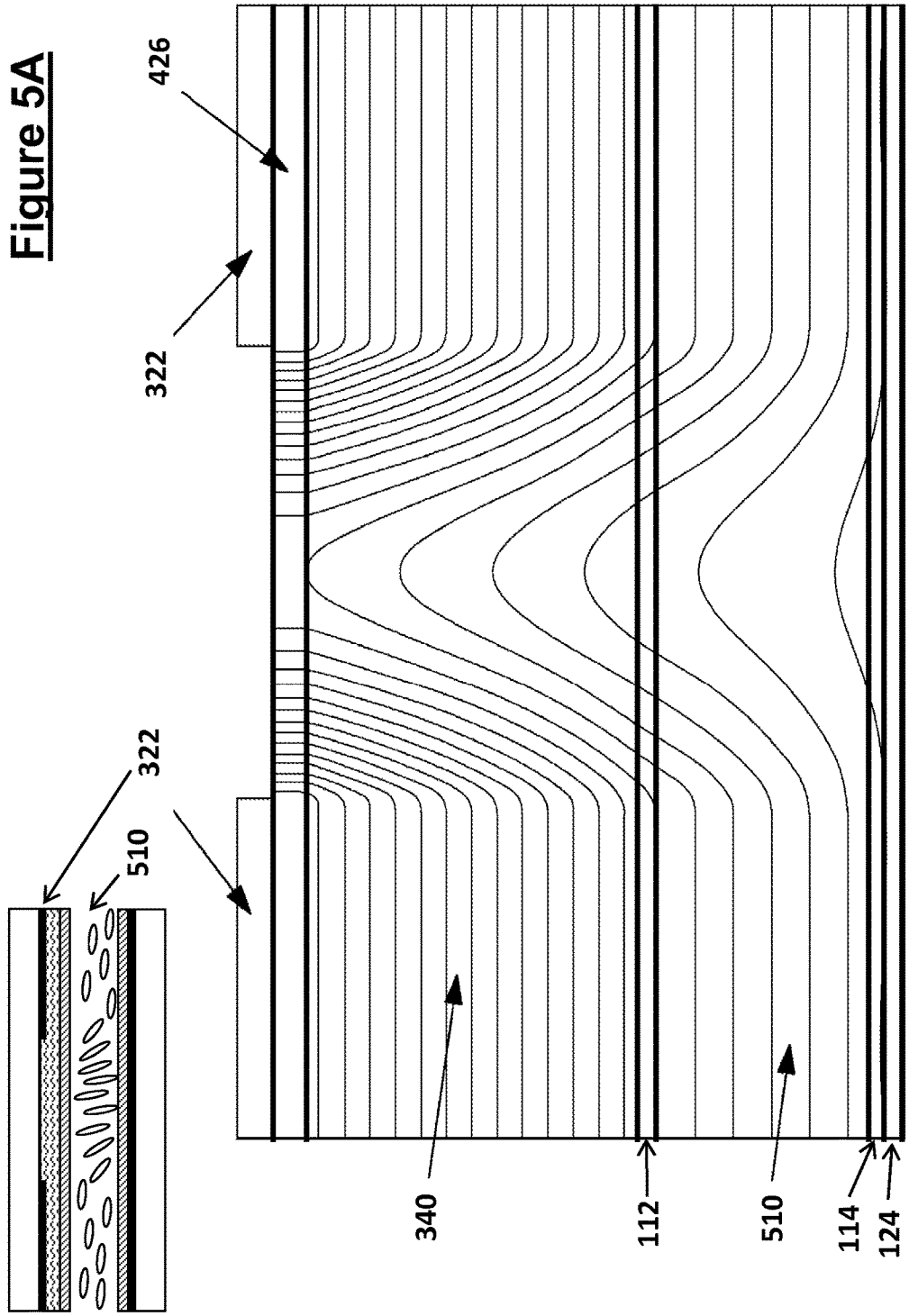
FIG. 5A is a schematic diagram illustrating an equipotentials distribution for a tunable liquid crystal lens subjected to a spatially modulated electric field in accordance with the proposed solution.

With reference to voltage amplitude modulation providing optical power variability illustrated for example in FIG. 3, the application of a drive signal across electrodes 124, 322 of TLCL 400 having an amplitude around Vmax creates a spatially modulated electric field of high variability having equipotentials illustrated in FIG. 5A. The inset depicts a highly variable LC molecular orientation and therefore the TLCL has a high optical power. The application of a drive signal across electrodes 124, 322 of TLCL 400 having an amplitude around Va creates an electric field of low variability having equipotentials illustrated in FIG. 5B. The inset illustrates LC molecular orientation of low variability and therefore the TLCL has a low optical power. It is noted that absence of an applied voltage drive signal brings the optical power to of the TLCL to a nominal value which may be used for example for far field observation.

Frequency Modulation Equipotentials

The frequency dependent layer 426 is employed to dynamically create an effective electrode profile. For example, electric field shaping is dependent on the frequency of the drive signal, which determines the extent of charge penetration into the frequency dependent layer 426. At a high frequency, corresponding to low charge mobility, the geometry of the hole-patterned electrode 322 has a greater contribution to the way in which the gradient control layer shapes the electric field. However, at a low frequency, corresponding to high charge mobility, the frequency dependent layer 426 creates an effective electrode surface, and the electric field shaping control layer 428 shapes the electric field according to the overall electrode geometry resulting from hole-patterned electrode 322 and the frequency dependent layer 426.

With reference to the layered structure of FIG. 2B, a drive signal applied between the hole-patterned electrode 322 and the flat electrode layer 124 will, in the absence of any significant charge mobility in the frequency dependent layer 426, create a non-uniform electric field across the LC layer 510. This non-uniform field can, for example, give a lensing profile to LC layer 510 of a particular characteristic as described hereinabove. For example, FIGS. 5A and 5B illustrate corresponding equi-potential planes for the layered geometry illustrated in FIG. 2B. As shown, in FIG. 5A, the use of a moderately high drive signal, for example 30 kHz at 30 Vrms, creates a moderate amount of charge movement in the frequency dependent layer 426 which generates a particular electric field, shown as having a smooth gradient. The active frequency range depends upon the characteristics of the frequency dependent material and the Vrms amplitude used. The inset illustrates LC molecular orientation having a high variability and therefore the TLCL has a high optical power.

However, when the driving signal applied has a low frequency for which there is a significant amount of charge mobility in the frequency dependent layer 426, the charge penetration into the frequency dependent layer 426 creates an effective electrode structure extending into the aperture 350 in the center of the hole-patterned electrode 322. An effective electrode is created which is substantially flat across the entire structure. This "horizontal" extension of the hole-patterned electrode 322 changes the electric field profile to be uniform as a result of the two effectively uniform electrode structures 322-426 and 124. This uniform field has a uniform orienting effect on the liquid crystal molecules so that any lensing effect is erased.

As shown in FIG. 5B, the use of a relatively low frequency driving signal, for example 1 kHz at 20 Vrms, results in greater charge penetration into the frequency dependent layer 426. This flattens the electric field profile, introducing correspondingly uniform LC molecular reorientation. The flat equi-potential surfaces correspond to a flat electric field across the diameter of the lens. Here also, the "low" frequency range depends upon the characteristics of the frequency dependent material used. The inset illustrates LC molecular orientation of low variability and therefore the TLCL has a low optical power.

It has been discovered that the use of relatively low frequency drive signals reduces disclinations (orientation defects). Use of flat electric field profiles provided by low frequency drive signals allow the "erasure" of a lens. Therefore lens erasure may be provided at low frequency and low RMS voltages without necessitating additional electrodes or a drastic change in the driving voltage to very low (e.g., 0 Volts) or very high voltages (e.g., 100 Volts), which tend to reduce TLCL performance or violate voltage limits of a host device, such as an intraocular TLCL prosthesis.

It is understood, that the experimental results presented hereinabove provide reduction to practice at high optical powers, however for intraocular TLCL prostheses lower Vrms curves illustrated in FIG. 4B are used with maximum Vrms amplitudes below 10V and frequencies in the order of 10 kHz.

Bipolar TLCL

In the above, extensive reference has been made to variable optical power TLCLs having unipolar (only positive or negative) optical power variability for example illustrated in FIGS. 3, 4A and 4B. It is understood that TLCLs 300/400/500 can be manufactured or operated to exhibit both negative and positive optical power variability. For certainty, the invention is not limited unipolar TLCLs.

Figure 7:
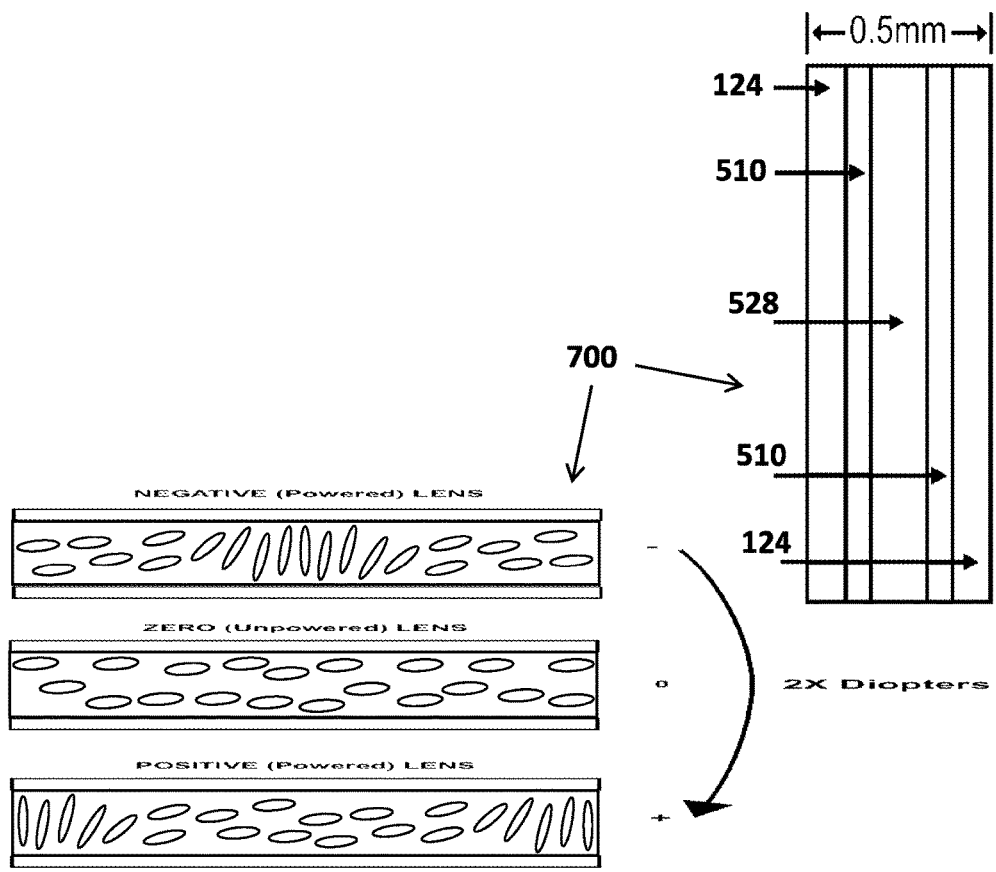
FIG. 7 is a schematic diagram illustrating a distribution of liquid crystal molecular orientations during bipolar operation of a tunable liquid crystal lens in accordance with the proposed solution.

FIG. 7 schematically illustrates bipolar operation of a LC layer 510. Co-pending commonly assigned U.S. Provisional Patent Application 61/441,647 entitled "Bipolar Tunable Liquid Crystal Lens Optical Device and Methods of Operating Thereof" describes differential drive signal application across full TLCL structures 700 for example shown in (the inset of) FIG. 7.

Tunable Optical Device System

In accordance with the proposed solution, the variable optical power response of a TLC lens is employed to create an intraocular TLCL prosthesis with variable optical power. Optical power can be varied between a minimum and a maximum by employing a mixed frequency and amplitude control responsive to a stimulus signal.

Figure 8:
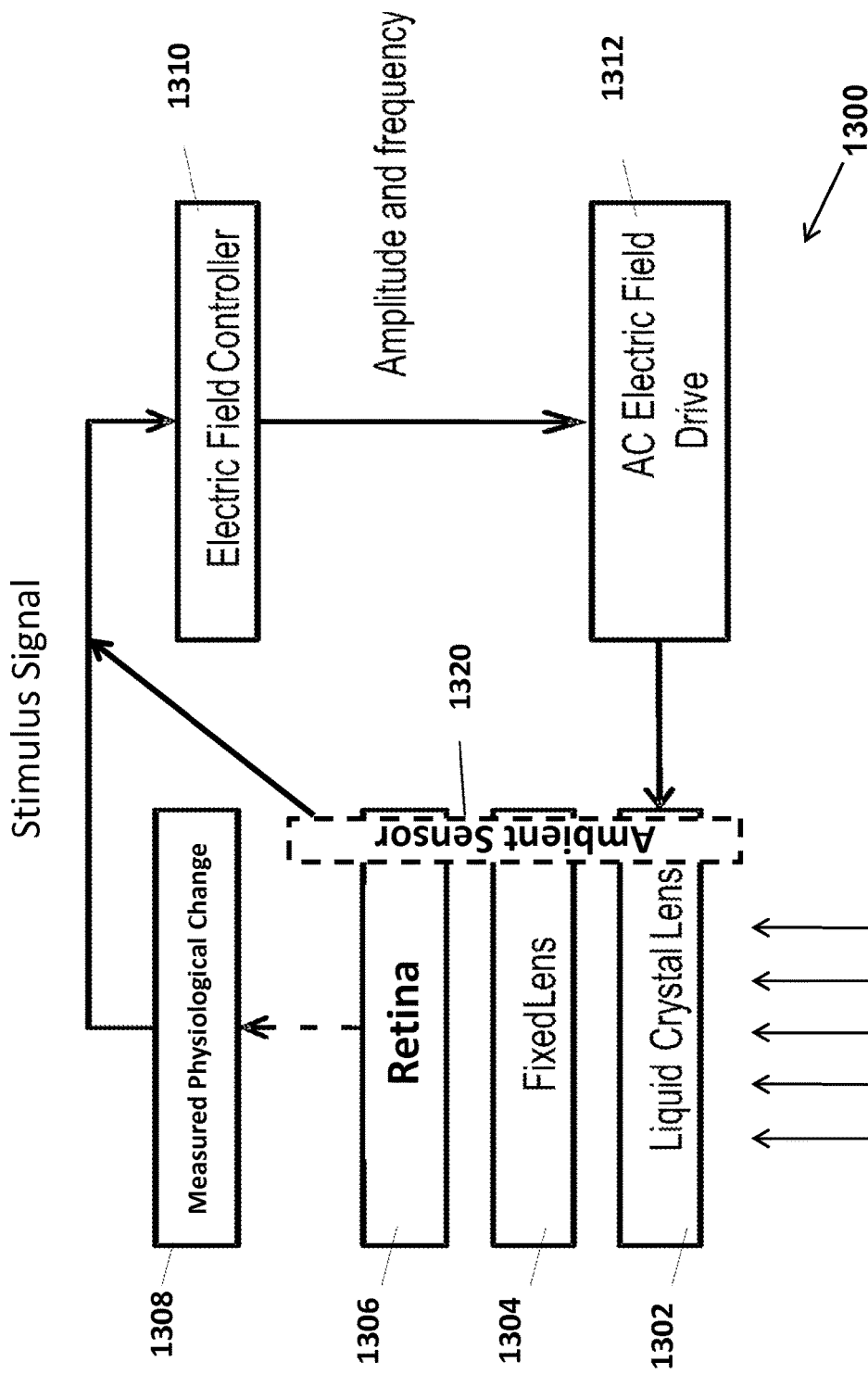
FIG. 8 is a schematic functional diagram showing interconnected tunable liquid crystal lens control components of an optical system providing assisted focus adjustment functionality in accordance with the proposed solution.

The control drive signal for tuning the TLCL can be provided by control signal electronics 1300 configured to cause the TLCL to control light propagation as a function of at least one measured physiological change and/or at least one environmental condition. As an example, an intraocular TLCL control system is schematically illustrated in FIG. 8 to have a TLC lens 1302 optionally combined with at least one fixed lens element 1304 to focus an image onto retina 1306 of the eye with the TLC lens 1302 providing focus control. The perceived image either causes a measurable physiological change (1308), for example involuntary muscle tension, and/or a physiological change caused via a voluntary (conscious) act, for example lid movement, squinting, etc. A transducer 1308 is employed to detect the physiological change, for example a pressure, tensile, stress, etc. sensor can measure muscle compression, tension, deflection etc. It is appreciated that a ciliary muscle plays a part in natural accommodation and the physiological change transducer 1308 can be configured to monitor the ciliary muscle of the eye. However, the invention is not limited to measuring physiological changes in the ciliary muscle, a variety of muscles intraocular or external can be used, for example muscles associated with the eyelid. Transducer 1308 provides a stimulus signal. It is appreciated that physiological changes such as squinting can be involuntary for example induced by a light intensity change separate from scene changes. An ambient (external) sensor 1320, providing an additional stimulus, can be employed to augment/correct the stimulus signal provided by the transducer 1308 (for example to provide a weighting factor).

An electric field controller 1310 translates at least one stimulus into at least one electrical drive signal parameter. Without limiting the invention, the electric field controller 1310 can employ lookup tables in performing its overall function, or at least as such a translation function relates to taking into consideration empirical information regarding the TLC lens 1302 and the general optical system, including but not limited to external sensor stimuli. For an intraocular TLCL prosthesis replacing the natural lens, the external sensor can be configured to take into consideration the effect of the variable iris of the eye and/or the electric field controller 1310 can be configured to take into account typical time variant iris variability (for example time variant calibration curves can be employed via lookup tables). For example time variant natural iris variability information can be employed to adjust the response of the electric field controller 1310 to prevent positive feedback situations unnecessarily driving the TLCL lens to extremes. It is expected that the natural reaction of the natural iris (and the nervous system controlling the iris) is plastic and that the iris will also react to operational particulars of the TLCL intraocular implanted prosthesis. The ambient sensor 1320 is illustrated in FIG. 8 to be in the optical path, for example behind the iris. The invention is not limited to a TLCL intraocular prosthesis replacing the natural lens of the eye, implantation of a TLCL in other eye cavities places the TLCL either in front or behind the iris and therefore the location of the ambient sensor 1320 can be varied accordingly. As another example, the physiological change sensor 1308 and/or ambient sensor 1320 can be replaced by an image sensor pointed towards the retina of the eye and receiving backscattered light from the retina. With only a limited number of pixels, such a sensor can be configured to detect sharpness in an image projected onto the retina, the image sensor proving a focus score as a stimulus signal.

An electric field drive circuit 1312 converts the electrical parameters into at least one drive signal to be applied to the TLCL 1302. Those skilled in the art would appreciate that component 1310, without limiting the invention, can be implemented using microcode executed on a microcontroller, while component 1312 can include voltage sources switched under the control of a microcontroller to provide a resulting drive signal of desired frequencies and RMS voltages. Such a microcontroller can be configured to obtain stimuli and determine drive signal parameters to operate the TLCL 1302 to change optical power towards best focus. For example best focus can be asserted by detecting minimal stimulus signal change below a threshold.

Frequency signal generators are known, and only limited details are provided herein with respect to employing such a frequency signal generator to implement a TLCL control component of a tunable optical system. For example, in order to provide low power operation, a miniature frequency generator can include a voltage boost circuit and an "H" bridge circuit having several (4) MOSFETs. The power consumption of such a circuit is estimated using typical efficiency numbers from commercially available components and found not to violate operational parameters for an intraocular prosthesis. The power dissipated by the MOSFET switches have three components; static power, dynamic power and load power. Static power is the sum of all biasing components. Dynamic power is the charge and discharge of the MOSFET gate capacitance and the load power is the power dissipated across the MOSFET's drain and source terminals (Imax*RDS(on)). Assuming the availability of a low voltage power source for controlling drive signal amplitude, voltage can be boosted by either using a switched capacitor ("charge pump") circuit or an inductive circuit. In either case the efficiencies for commercially available products are found to be similar and within operational parameters. Inductive boost offers some advantages over the charge pump.

Implementations of Intraocular TLCL Prostheses

By way of a non-limiting example and with reference to FIG. 2C for a full TLCL, with reference to FIG. 6 for dual full TLCL 600 and with reference to FIG. 7 for bipolar full TLCL 700, the geometry of an intraocular variable optical power flat TLC lens implemented in accordance with the proposed solution are provided. Suitable biocompatible/non-toxic materials have been tested and are assumed in the following. Thermal cycling tests confirm long term storage and have shown compatibility with sterilization requirements while retaining operability. Experimental tests have shown long life times measured in years. It will be appreciated that TLCL intraocular optical devices can be fabricated using layer-by-layer assembly and, preferentially, in a parallel way (many units simultaneously, called "wafer level"), the final product being obtained by singulation and, optionally, joining single TLCLs with operation axes (directors) in cross (orthogonal) directions to focus both orthogonal polarizations of light into full TLCLs. While TLCLs configured in accordance with the above disclosure exceed the required operational parameters of an intraocular TLCL prosthesis, it will be appreciated that miniaturization and low power operability of such TLCLs in an adaptive intraocular prosthesis is subject to greatly varying dimensions depending on geometry, choice of materials, and particularly depending on tradeoffs between operational parameters:

Assuming a 20-20 vision prior to removal of a natural lens for example during a cataract operation in an adult, an optical power range of 3 diopters, while limited compared to the juvenile accommodation range, typically can provide sufficient optical power variability to permit a focus range spanning from infinity to about 30 cm. An optical power range greater than 3 diopters can provide closer focus and/or increased ability to correct imperfect vision. For example, 2.5 diopters can be useful for correcting presbyopia. Thus depending the visual condition which is to be addressed, different adaptive accommodation is required and therefore different optical range variability is required.

For example, the (dual) full TLCL structure (600) 500 can be configured to focus at infinity employing maximum optical power and at a closest focusing distance employing minimum optical power. Depending on whether the TLCL is configured as a positive lens or a negative lens, infinity focus or closest focus can correspond to maximum power drive or minimum power drive. The configuration may depend on factors such as focusing ability of the eye prior to surgery, selected mode of driving the TLCL, etc. Alternatively, without limiting the invention, employing a bipolar TLCL 700 infinity focus can be provided by driving the TLCL at maximum optical power of one polarity, closest focus can be provided by driving the TLCL at maximum optical power of the other polarity, and focus at a working/reading distance/arm's length can be provided employing zero optical power adjustment.

The typical available capsular bag size following natural lens removal is about 9 mm in diameter and 4 mm in thickness (anterior to posterior dimension). FIG. 5 illustrates a 0.5 mm thick flat full TLCL 500, FIG. 6 illustrates a 1 mm flat dual full TLCL 600 while FIG. 7 illustrates a 0.5 mm thick flat bipolar TLCL 700 employing 100 μm glass substrates 124. For example, TLCLs having an accommodative clear aperture 360 of about 4.5 mm can provide at least 1.7 diopters employing a single flat full TLCL 500, at least 3.5 diopters employing a dual flat full TLCL 600, and at least 7 diopters employing a flat bipolar full TLCL 700. A 4.5 mm accommodative clear aperture 360 benefits from relatively small incisions. Larger accommodative clear apertures 360 while permitting operation in lower light conditions would require larger incisions and/or foldable TLCL structure however at reduced optical power. For example a 6 mm accommodative clear aperture 360 would provide roughly half the optical power of a TLCL having 4.5 mm accommodative clear aperture 360. Even at 6 mm accommodative clear aperture, sufficient structural material reserve around the clear aperture 350 can be provided to ensure operability without violating capsular bag dimensions. Conversely, smaller accommodative clear apertures 360 benefit from requiring smaller incisions and operation at higher optical powers. For example, TLCLs having an accommodative clear aperture 360 of about 3 mm can provide at least 3.5 diopters employing a single flat full TLCL 500, at least 7 diopters employing a dual flat full TLCL 600, and at least 14 diopters employing a flat bipolar full TLCL 700 providing greater coverage of the juvenile accommodation range. Smaller accommodative clear apertures 360 while providing increased optical power can restrict light throughput. Light throughput can be increased by expanding light transmittance of the TLCL structure layers and/or that of any encapsulating material. For example, employing more flexible thinner single full TLCL 500 or single bipolar full TLCL 700 allows at least 90% transmittance. Less flexible thicker dual full TLCL 600 allows at least 80% transmittance. Reducing the thickness of some layers can reduce transmittance depending on material/physical properties layer material.

Top and bottom alignment layers 112/114 can include Polyimide layers about 20 nm thick that are rubbed to yield surfaces which induce a liquid crystal ground state alignment with a low pre-tilt angle, for example 3°. For example, the liquid crystal layer 510 can be 5 to 30 μm thick, with larger thicknesses providing greater optical power. Thicker liquid crystal layers 510 tend to require higher operating temperatures and drive signal power.

The hole-patterned electrode 322 can be made of an opaque metal such as Aluminum (Al), or it can be made of Indium Tin Oxide (ITO) which is transparent. The thickness of the hole-patterned electrode 322 can be about 10 nm. Without limiting the invention, the hole-patterned electrode layer 322 can also be substantially optically hidden and thus would not interfere with the propagation of light through the optical device.

The weakly conductive layer 426 can have a thickness of about 10 nm. The frequency dependent (permitivity or complex dielectric) material of the WCL 426 can comprise a variety of materials such as, but not limited to, titanium oxide. Titanium oxide has semiconductor properties that change with applied drive signal frequency.

In the embodiment of FIG. 2C, a hole-patterned electrode 522 and frequency dependent material 526 form a single variable conductivity layer 528 shared between two LC layers 510 reducing thickness.

In accordance with a preferred embodiment of the proposed solution, substrates 124 include a degree of flexibility permitting the TLCL 500/600/700 to bend and thus the use of an incision of reduced size. The above assume 100 μm thick glass substrates. Greater flexibility can be achieved in dual TLCL structures by eliminating one of the central glass substrates 124 see, FIG. 6, or by employing thinner substrates 124. Substrates 124 can be as thin as 50 μm which combined with compliant (pliable) adhesives can provide a useful amount of flexibility and reduce incision size. Alternatively, incision size can be further reduced by employing a flat TLCL 500/600/700 having a circular outer shape. While typical TLCLs are wafer level manufactured and singulated employing standard scribe and dicing techniques into individual squares, laser cutting techniques have been successfully tested to singulate circular intraocular TLCLs.

Alternatively, the flat (dual) full TLCL structure (600) 500 can be encapsulated in a lenticular body which represents the intraocular prosthesis. A lenticular body of a substantially spheroidal outer shape can be employed as illustrated in FIG. 9A. It is appreciated that the natural lens and capsular bag are not necessarily symmetric.

If the natural eye prior to natural lens removal is not 20-20, then a baseline correction can be provided by employing a combination of a lenticular body shape configured to have a composition and an index of refraction. FIGS. 9B and 9C illustrate encapsulated TLCLs having additional fixed optical power lens elements (non-tunable) deposited thereon. Either or both flat surfaces the TLCL can have a fixed optical element deposited thereon. A combination of the lenticular body and fixed optical power elements can be employed to shift or amplify accommodation range of the intraocular prosthesis. For example, if the fixed optical element provides +11 diopters and if the TLCL provides an accommodation of 7 diopters, then the optical power provided by such an intraocular TLCL prosthesis can change from 11 to 18 diopters.

Figure 10A:
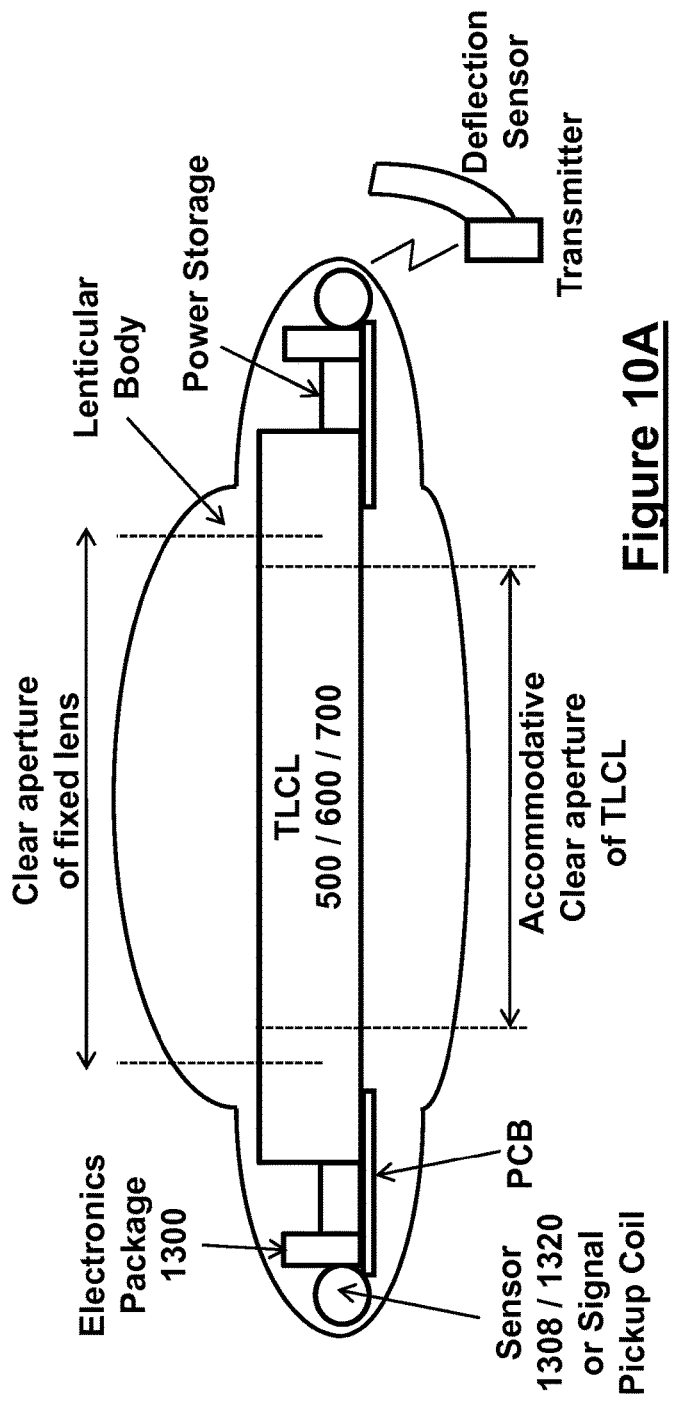
FIG. 10A is a schematic diagram illustrating a cross-section through an integral encapsulated tunable liquid crystal lens intraocular prosthesis in accordance with the proposed solution.
Figure 10B:
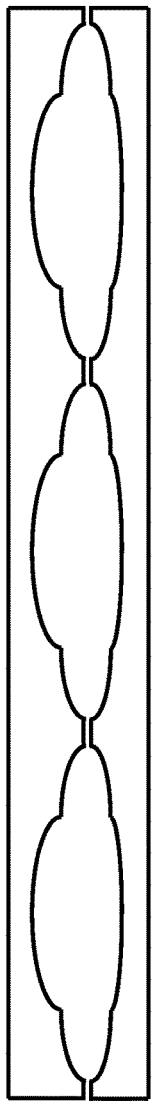
FIG. 10B is a schematic diagram illustrating a cross-section through a mold array for manufacturing encapsulated tunable liquid crystal lens intraocular prostheses in parallel in accordance with the proposed solution.
Figure 11:
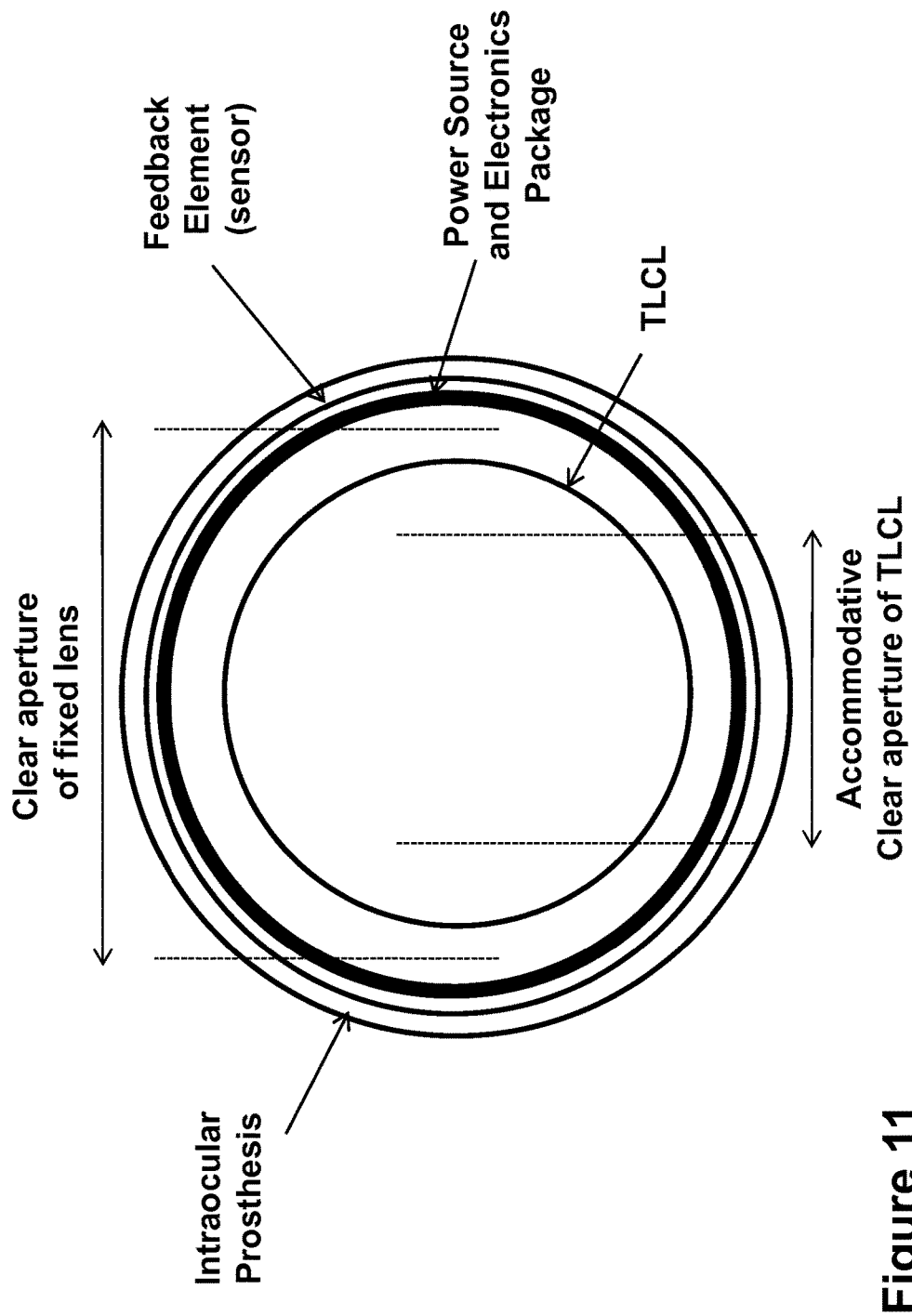
FIG. 11 is a schematic diagram illustrating a top view of an integral encapsulated tunable liquid crystal lens intraocular prosthesis in accordance with the proposed solution.

In accordance with some embodiments of the proposed solution, an integral intraocular prosthesis includes the TLCL 500/600/700, an electronics package 1300, and power storage on a flexible Printed Circuit Board (PCB), for example made of (biocompatible) Kapton™ (Kapton is a trademark of E. I. du Pont de Nemours and Company or its affiliates), the flexible PCB itself having a aperture. An example of such an integral intraocular prosthesis is illustrated in FIG. 10A to include encapsulating material forming a pronounced fixed optical power element over the TLCL and also encapsulating the electronics package 1300, and power storage. It is understood that FIG. 10A is highly schematic, the lobed shape provides high optical power fixed optical lens elements by employing pronounced lenticular shapes. In accordance with another implementation of the proposed solution, FIG. 11 illustrates a top view of integral intraocular prosthesis showing the power source and electronics package 1300 being disposed around the periphery of the intraocular prosthesis. The FIG. 10B illustrates a cross-sectional view of a mold for encapsulation in manufacturing an array of intraocular TLCL prostheses. The mold includes an array of reservoirs for holding encapsulating material.

With the sensor 1308 being disposed around the periphery of the intraocular TLCL implant, such an internal pressure sensor can be configured to detect external mechanical action exerted onto the capsular bag, for example by the ciliary muscle.

Alternatively, an external deflection sensor and transmitter are illustrated in FIG. 10A, external deflection sensor and transmitter which can be affixed to a muscle, not limited to the ciliary muscle, to measure physiological change in the form of muscle action and to transmit a stimulus signal to a pickup coil in the intraocular prosthesis. Muscles of the eyelid are other examples. Eyelid muscles have the advantage that they can be consciously controlled besides being autonomously/instinctively controlled by the body. For example the deflection sensor can include a piezo element. A number of piezo element arrangements can be configured to react to muscular bend, contraction, etc. and provide a feedback stimulus signal. Such piezo elements are compatible with any muscular environment in the vicinity of the eye including facial muscles about 1 cm away from the eye.

Figure 12A:
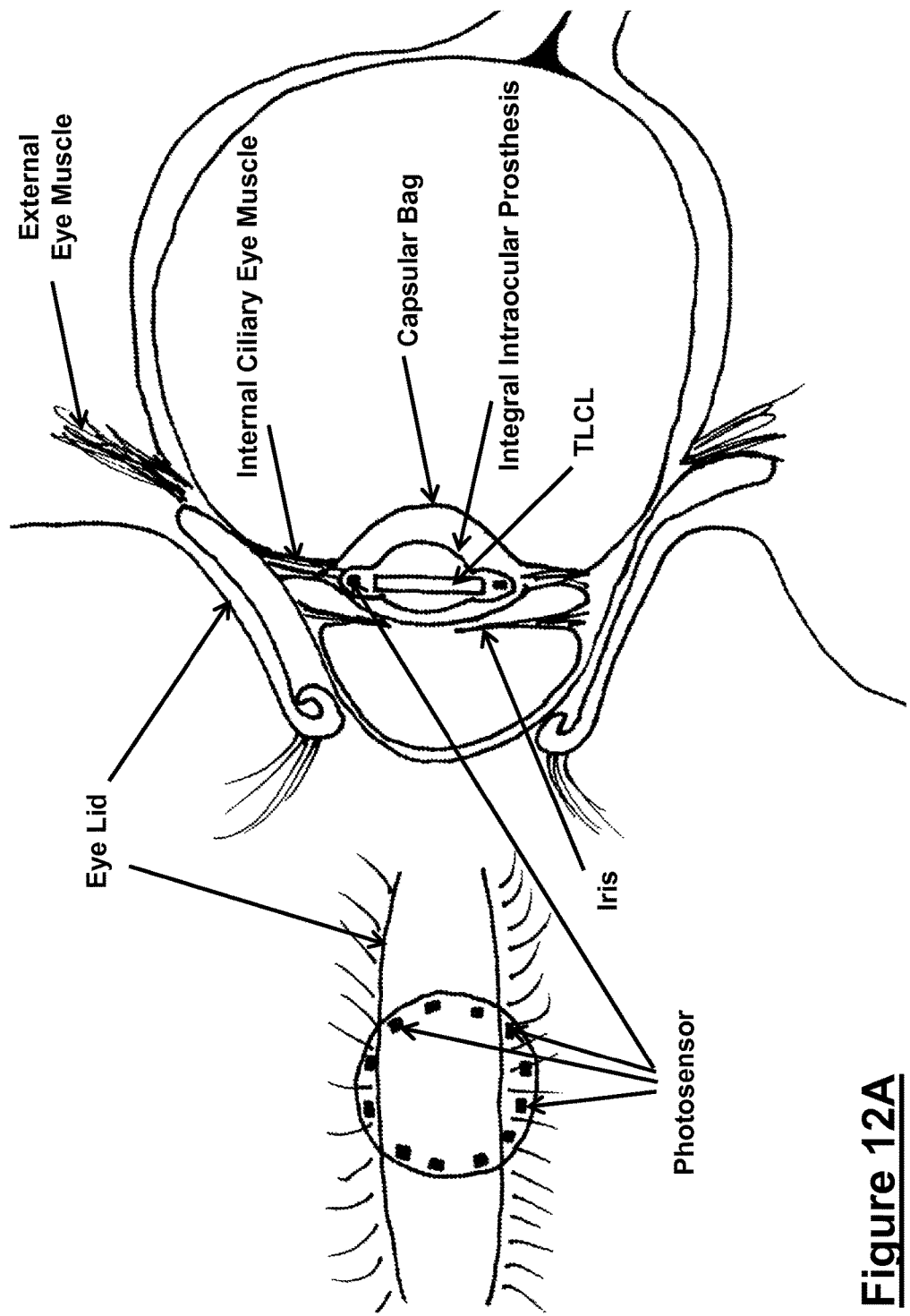
FIGS. 12A and 12B are schematic diagrams illustrating integral intraocular prostheses detecting physiological changes outside an eye.
Figure 12B:
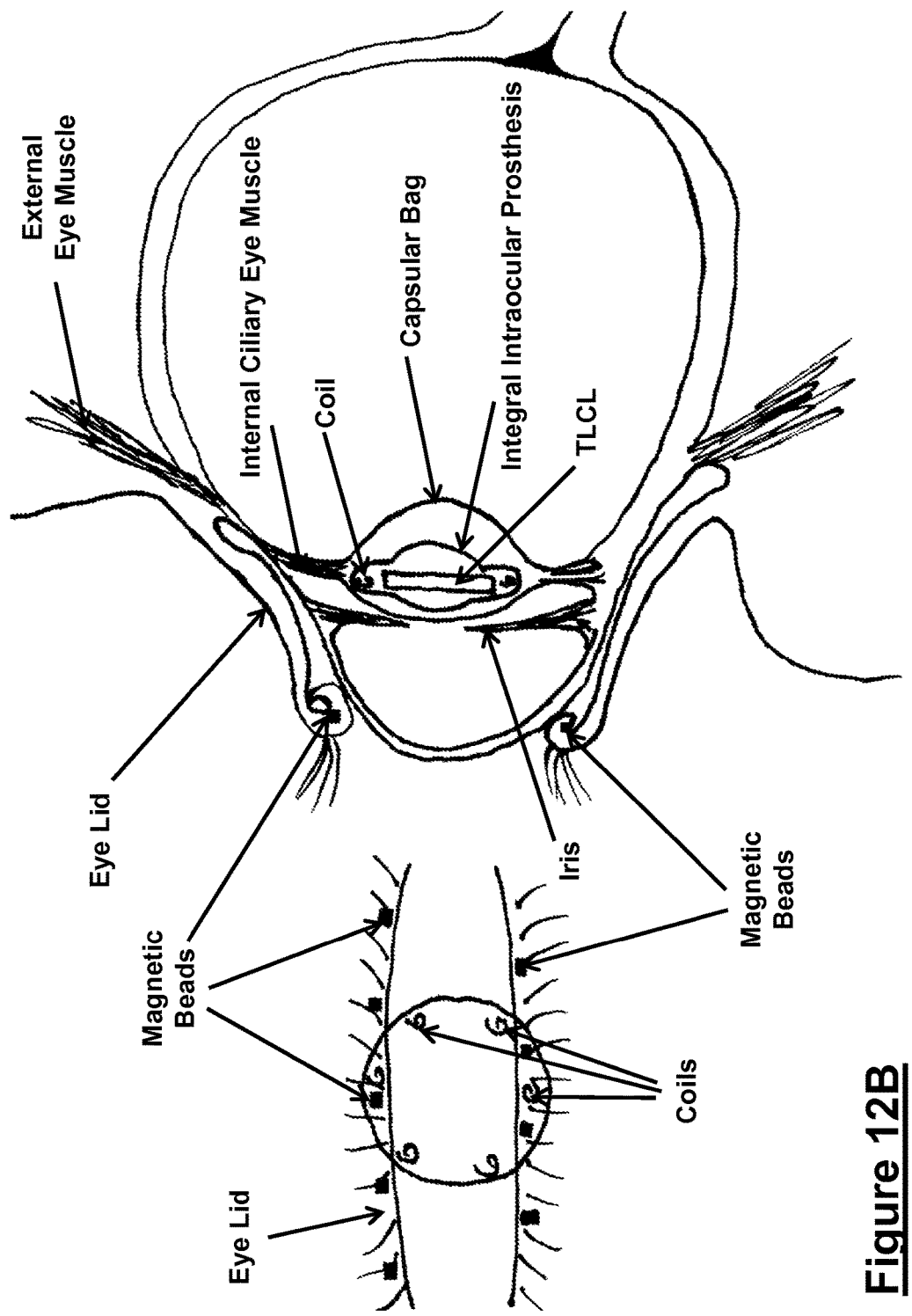

For certainty, external physiological change measurements do not necessarily have to be transmitted. FIGS. 12A and 12B (not anatomical) schematically illustrate integral intraocular prostheses detecting physiological changes outside the eye. Advantages are derived from a low power integral intraocular device.

In accordance with one implementation, sensor 1320 includes at least one, typically a number of photosensors disposed around the TLCL for detecting the position of the eyelid. FIG. 12A illustrates the location of the photosensors, the inset illustrates an example of a photosensor distribution around the integral intraocular TLCL prosthesis. The greater the accommodative clear aperture 360 employed, the more the photosensors 1308 spend time behind the iris for an intraocular TLCL prosthesis implanted in the capsular bag. The inset of FIG. 12A illustrates the relative position of the eyelid with respect to the photosensors during a blink or squint. A blink can be differentiated from a squint for example by low rate sampling which statistically miss a blink or by long term integration of light falling onto the photosensors. The position of the eyelid can be inferred from the pattern of light measurements. It can be appreciated that no additional procedure, aside from that replacing the natural eye lens with the integral intraocular TLCL prosthesis, is necessary in employing this implementation.

In accordance with another implementation of the proposed solution, the physiological change sensor 1308 includes at least one coil, typically a number of coils sensitive to varying magnetic fields. At least one magnetic bead, typically a number of magnetic beads, for example including niobium each, encapsulated in a biocompatible material can be implanted for example via injection into the rim of the eyelid FIG. 12B. The human eye does not sit still moving involuntarily in random directions at a frequency range 30 to 70 times per second. The coil(s) can pick up magnetic field variations induced by both eyelid action and involuntary eye movement, and determine the degree of closure of the eyelid which can then be provided as a stimulus signal. Employing a number of magnetic beads the orientation of the eye within the eye socket can be taken into account. Dual intraocular prostheses can share eye orientation information, for example to determine focusing distance from angle of view measurements.

In accordance with the proposed solution, in operation the stimulus signal is generated from measurements. For example, if the eyelid is closed then the TLCL lens is powered down; if the person is squinting then the TLCL is caused to focus at infinity (powered or unpowered), if not squinting/relaxed/opened up then TLCL is caused to provide high optical power (powered or unpowered). A variety of other eyelid gestures can be employed, without limiting the invention thereto.

In accordance with an implementation of the proposed solution, eyelid gestures may be distinguished therebetween and employed to operate the intraocular implant. For example, calibration can employ a test pattern at a particular distance from the eye employing eyelid gestures to accept/deny/increase/decrease etc.

The power storage can include a battery or a capacitor. With respect to the power source, it would be appreciated that integral intraocular prostheses are limited to low power implementations. For example, a 5V battery or capacitor can be employed providing sufficient operational duration. For example, for a 3.0 mm accommodative clear aperture 360 implementation a full TLCL 500 would consume 0.035 mW while total power consumption, for both TLCL and electronics package 1300, is around 0.20 mW. A dual full TLCL 600 having a 4.5 mm accommodative clear aperture 360 would consume 0.157 mW with a total power consumption of about 1.35 mW. Lower power operation is possible as a tradeoff against other intraocular prosthesis operational parameters.

It is noted that the TLCL appears in an electrical circuit as a capacitive load. For example, at 7V/10 kHz operation, a full TLCL 500 having a 3.0 mm accommodative clear aperture 360 has a typical capacitance of about 70 pF, while a dual full TLCL 600 having a 4.5 mm accommodative clear aperture 360 has a typical capacitance of about 320 pF. Lower voltage operation is possible however fast optical power transition times favor high voltage operation. For example, 7V operation can provide optical power transition times of about 0.4 s but can vary between 0.2 s and 0.6 s.

Figure 16:
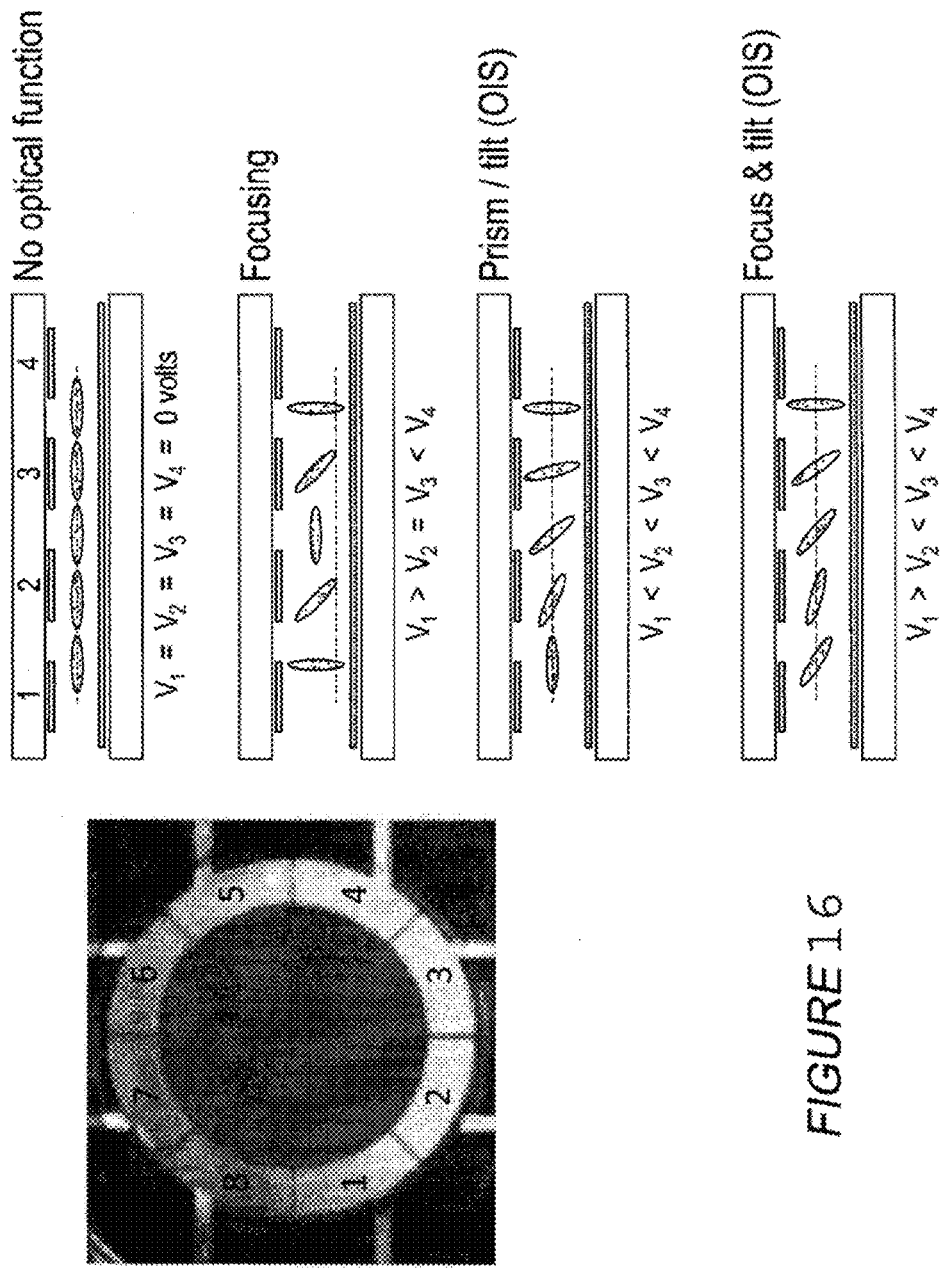
FIG. 16 shows an image of eight separated arc shaped electrode segments forming a ring electrode in a tunable liquid crystal circular aperture lens along with four different LC layer refractive index distributions, wherein similar features bear similar labels throughout the drawings. While the layer sequence described is of significance, reference to "top" and "bottom" qualifiers in the present specification is made solely with reference to the orientation of the drawings as presented in the application and do not imply any absolute spatial orientation.

Optical error correction of aberrations, astigmatism, coma, etc. can also be implemented in an integral intraocular prosthesis employing a parametric TLCL structure having segmented electrodes, as illustrated in FIG. 16 that shows eight separated arc shaped electrode segments forming a ring electrode. By varying only the voltage amplitudes of common frequency control drive signal components fed to the segments, a complex electric field spatial modulation can be provided. Alternatively, the complex electric field spatial modulation can be provided by varying the frequencies of the drive signal components fed to the segments. For example Tunable Liquid Crystal Lenses having a movable optical axis are described in co-pending commonly assigned International Patent Application PCT/CA/2010/002023 entitled "Image Stabilization and Shifting in a Liquid Crystal Lens" claiming priority from commonly assigned U.S. Provisional Patent Application 61/289,995 entitled "Image Stabilization And Shifting In A Liquid Crystal Lens" filed Dec. 13, 2009, the entirety of which is incorporated herein by reference. commonly assigned U.S. Patent Application 61/410,345 entitled "Methods of Adjustment Free Manufacture of Focus Free Camera Modules" filed 4 Nov. 2010, which is incorporated herein by reference, describes accounting for overall optical system optical error/aberration during TLCL manufacture.

Figure 13:
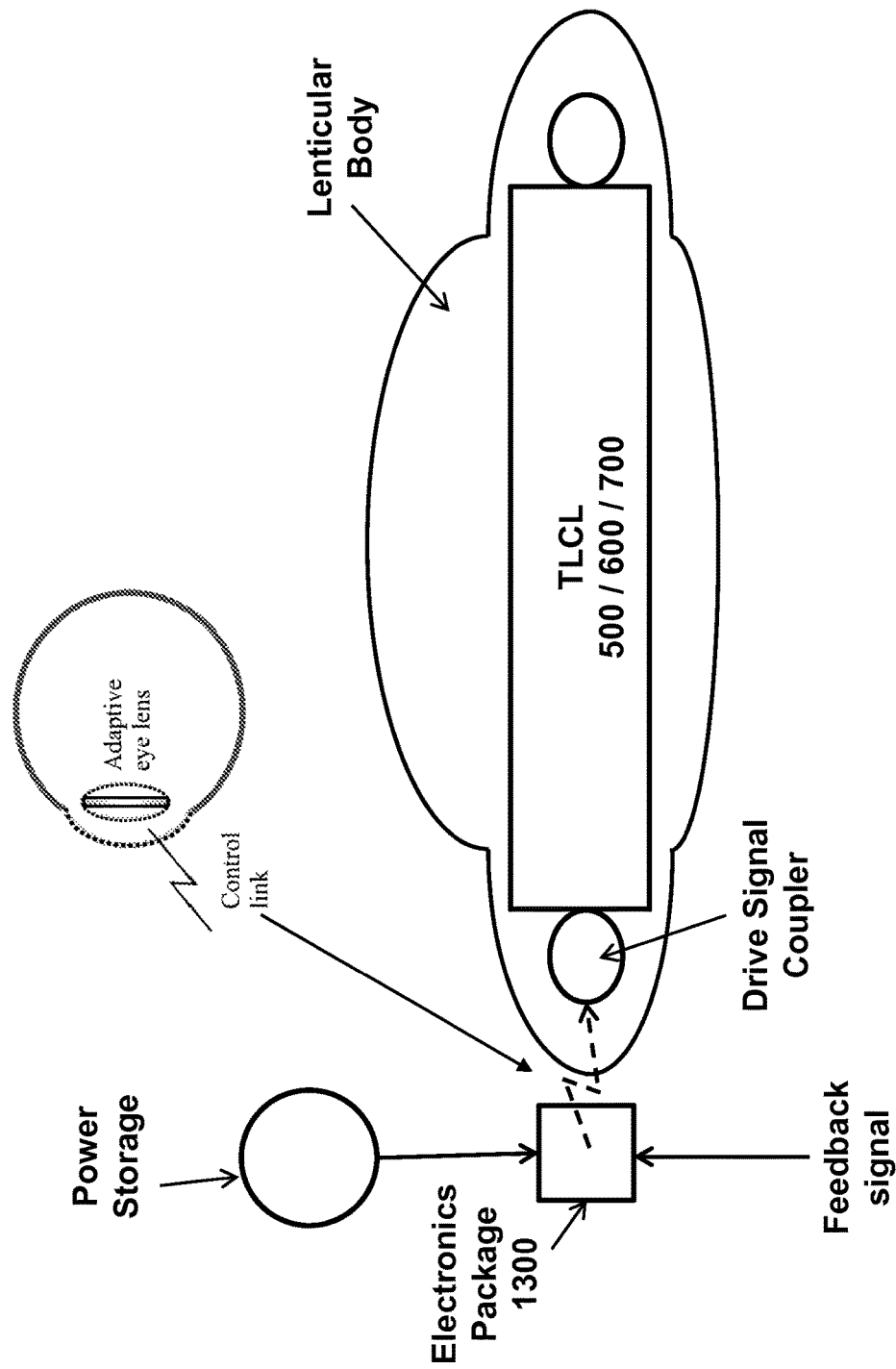
FIG. 13 is a schematic diagram illustrating an intraocular prosthesis having an external electronics package, the inset showing wireless control, in accordance with the proposed solution.
Figure 14:
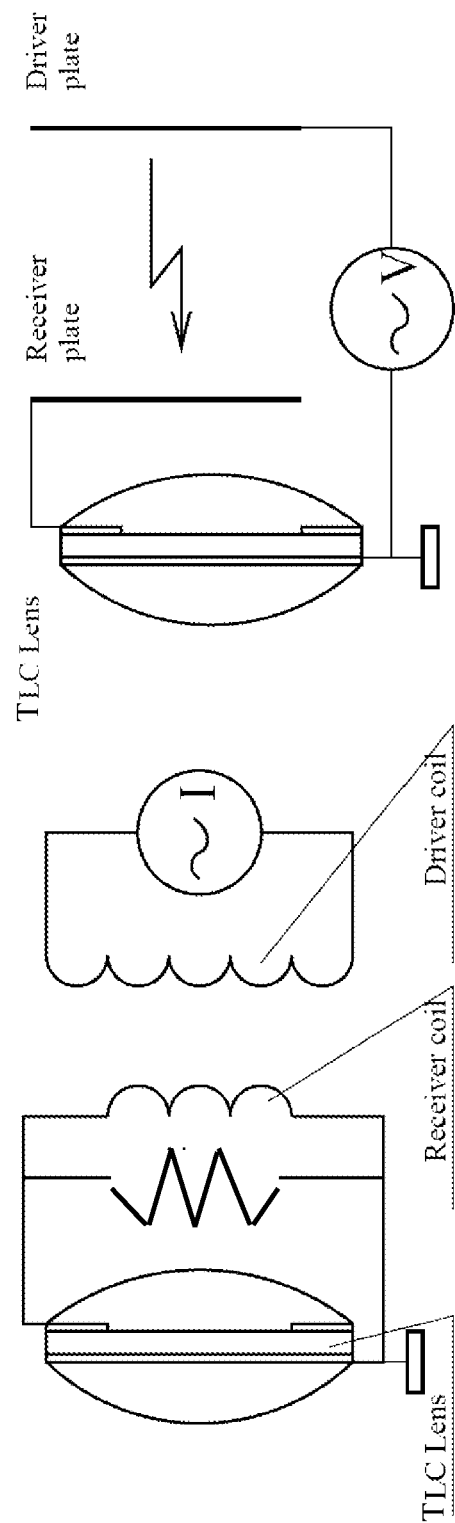
FIGS. 14A and 14B illustrate wireless inductive and capacitive drive respectively in accordance with the proposed solution.
Figure 15:
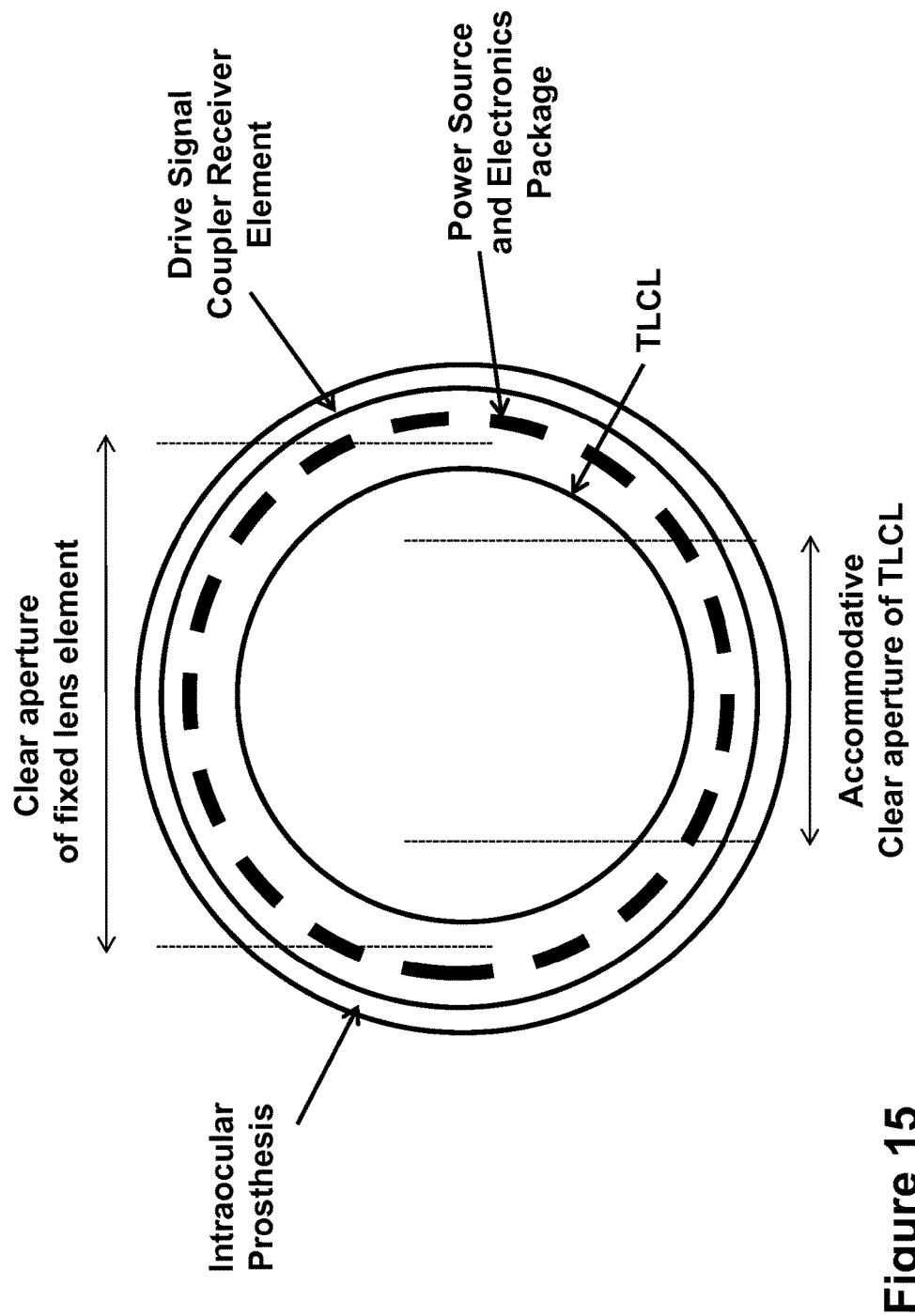
FIG. 15 is a schematic diagram illustrating the location of a drive signal receiver element of a drive signal coupler in accordance with the proposed solution.

FIG. 13 illustrates another embodiment of the proposed solution wherein the electronics package is external, for example incorporated in an eye glasses frame (not shown). FIGS. 14A and 14B illustrate examples of wireless TLCL drive employing a drive signal coupler. FIG. 14A illustrates inductive drive coupling employed with the TLCL connected as a capacitor in an LRC resonant circuit. FIG. 14B illustrates capacitive drive coupling. It is understood that FIGS. 14A and 14B are electronic schematics: for certainty, the "receiver plate" in FIG. 14B need not be a component separate from the intraocular prosthesis and the fixed optical elements need not extend to the edges of the intraocular prosthesis. TLCL edges contain electrode layer contacts and require encapsulation. FIG. 15 illustrates the location of the integrated receiver coil/receiver plate of the drive signal coupler receiver element. It is understood that such a signal receiver element can also be used as a receiver element of a power coupler to recharge the power source (shown dashed) of an integral intraocular prosthesis or retard its depletion. For example, an eye glasses frame or an eye patch can be employed in a similar fashion as illustrated in FIG. 14A or 14B to recharge the power store (battery or capacitor) either during operation or at night. Such eye glasses frame or eye patch includes an external transmit element for transmitting power.

Those skilled in the art will recognize that the various principles and embodiments described herein may also be mixed and matched to create a TLC lens optical devices with various auto-focus characteristics. Electrodes of different shapes and configurations; frequency dependent materials of different types, shapes and positions; dual frequency liquid crystal materials of different types; different drive signal generators; etc. can be used in combination to create a TLC lens optical device with a particular characteristic. The TLC lens devices may be frequency controlled, voltage controlled, or controlled by a combination of the two.

While the invention has been shown and described with referenced to preferred embodiments thereof, it will be recognized by those skilled in the art that various changes in form and detail may be made therein without departing from the spirit and scope of the invention as defined by the appended claims.

What is claimed is:

1. An intraocular implant apparatus for replacing a natural lens of an eye, the apparatus comprising:
    an encapsulated tunable liquid crystal optical device including:
        a tunable liquid crystal lens having a variable optical power provided by a liquid crystal layer having a spatially non-uniform variable refractive index over an accommodation clear aperture, said liquid crystal layer being sandwiched between:
            a hole patterned ring electrode structure formed by a plurality of separated arc shaped electrodes arranged end to end about said accommodation clear aperture; and
            a flat electrode;
        a tunable liquid crystal lens drive signal generator configured to generate a drive signal component to drive individually each of said arc shaped electrodes with respect to said flat electrode of said tunable liquid crystal lens;
        a tunable liquid crystal lens controller configured to control said drive signal generator to change said tunable liquid crystal lens optical power and to provide optical error correction in response to a stimulus signal;
        power store configured to store electrical power to drive said tunable liquid crystal lens and said controller; and
        a sensor component configured to provide said stimulus signal; and
    a substantially transparent encapsulating material configured to provide a fixed optical power element for augmenting said optical power of said tunable liquid crystal lens, said encapsulating material forming a pronounced lenticular shape at least over said accommodation clear aperture of the tunable liquid crystal lens, said encapsulating material encapsulating said drive signal generator, tunable liquid crystal lens controller, said power storage and said sensor component arranged about a periphery of said tunable liquid crystal lens.

2. An apparatus as claimed in claim 1, said optical power of said tunable liquid crystal lens being variable within a range, and said fixed optical power element being configured to shift said optical power variability range of said tunable liquid crystal lens.

3. An apparatus as claimed in claim 1, said encapsulated optical device being configured to fold for insertion into a region of said eye via an incision having at least one dimension smaller than a corresponding unfolded dimensions of said optical device.

4. An apparatus as claimed in claim 1, said encapsulated optical device being one of sized to fit into a capsular bag of said natural lens and having outer dimensions smaller than dimensions of said natural lens.

5. An apparatus as claimed in claim 1, said optical device comprising a lens substrate deposited onto said tunable liquid crystal lens configured to at least one of augment said optical power of said tunable liquid crystal lens and shift said optical power variability range of said tunable liquid crystal lens.

6. An apparatus as claimed in claim 1, said tunable liquid crystal lens comprising a unipolar tunable liquid crystal lens configured to focus an image at infinity onto a retina of said eye under unpowered drive conditions and further configured to focus a near image onto said retina under high power drive conditions.

7. An apparatus as claimed in claim 1, said tunable liquid crystal lens further comprising a bipolar tunable liquid crystal lens.

8. An apparatus as claimed in claim 7, said bipolar tunable liquid crystal lens being configured to focus one of a near image and an image at infinity onto a retina of said eye under a corresponding one of a negative optical power and a positive optical power high power drive conditions.

9. An apparatus as claimed in claim 7, said bipolar tunable liquid crystal lens being configured to focus an image substantially at one of an arm's length, reading distance and working distance onto said retina under unpowered drive conditions at zero optical power.

10. An apparatus as claimed in claim 1, in providing said stimulus signal said sensor component comprising an eye strain sensor configured to measure eye strain, and said tunable liquid crystal lens controller being configured to convert eye strain measurements into an optical power setting.

11. An apparatus as claimed in claim 10, said eye strain sensor further comprising a muscle tension sensor configured to measure eye strain by measuring muscle tension in a muscle.

12. An apparatus as claimed in claim 11, said muscle comprising a ciliary muscle.

13. An apparatus as claimed in claim 1, said sensor component comprising an eyelid activity sensor configured to detect, from within said optical device, a degree of closure of an eyelid of said eye in providing said stimulus signal, and said tunable liquid crystal lens controller being configured to convert said degree of lid closure into an optical power setting.

14. An apparatus as claimed in claim 13, said eyelid activity sensor being configured to detect an eyelid shut condition of said eyelid, and said tunable liquid crystal lens controller being configured to shut down said tunable liquid crystal lens in response to said eyelid shut condition.

15. An apparatus as claimed in claim 13, said eyelid activity sensor comprising at least one photosensor measuring light falling thereon.

16. An apparatus as claimed in claim 1 comprising:
a power coupler configured to capture and store transmitted power into said power storage; and
an external power source configured to transmit power.

17. An apparatus as claimed in claim 16, said power coupler device comprising a receiver element encapsulated into said optical device, said receiver element being configured to receive radiated power and further configured to convert said radiated power into electrical power for storage into said power storage.

18. An apparatus as claimed in claim 17, said external power source comprising an external transmit element in one of an eye glass frame and an eye patch.

19. An apparatus as claimed in claim 16, said power capture device comprising a resonant inductor encapsulated into said optical device, said inductor being configured to receive power by induction and configured to convert said induced power into electrical power for storage into said power storage.

20. An apparatus as claimed in claim 19, said inductor comprising an induction coil driven externally.

21. An apparatus as claimed in claim 1, said power storage further comprising one of a battery and a capacitor.

22. An apparatus as claimed in claim 21, said battery comprising a rechargeable battery.

* * * * *